US012729370B2

(12) United States Patent
Tran et al.

(10) Patent No.: US 12,729,370 B2
(45) Date of Patent: Sep. 8, 2026

(54) T CELL RECEPTORS SPECIFIC FOR A MUTANT FORM OF THE RET ONCOGENE AND USES THEREOF

(71) Applicant: Providence Health & Services—Oregon, Portland, OR (US)

(72) Inventors: Eric Tran, Portland, OR (US); Yi-Ping Shih, Portland, OR (US)

(73) Assignee: Providence Health & Services—Oregon, Portland, OR (US)

( * ) Notice: Subject to any disclaimer, the term of this patent is extended or adjusted under 35 U.S.C. 154(b) by 615 days.

(21) Appl. No.: 18/038,071

(22) PCT Filed: Nov. 23, 2021

(86) PCT No.: PCT/US2021/060482

§ 371 (c)(1),
(2) Date: May 22, 2023

(87) PCT Pub. No.: WO2022/115415

PCT Pub. Date: Jun. 2, 2022

(65) Prior Publication Data

US 2024/0002795 A1 Jan. 4, 2024

Related U.S. Application Data

(60) Provisional application No. 63/117,859, filed on Nov. 24, 2020.

(51) Int. Cl.

| | |
|---|---|
| ***C12N 5/0783*** | (2010.01) |
| ***A61K 35/17*** | (2025.01) |
| ***A61K 40/11*** | (2025.01) |
| ***A61K 40/19*** | (2025.01) |
| ***A61K 40/24*** | (2025.01) |
| ***A61K 40/31*** | (2025.01) |
| ***A61K 40/42*** | (2025.01) |
| ***C07K 14/705*** | (2006.01) |
| ***C12N 15/86*** | (2006.01) |
| *C07K 14/74* | (2006.01) |

(52) U.S. Cl.

CPC ............ *C12N 5/0636* (2013.01); *A61K 35/17* (2013.01); *A61K 40/11* (2025.01); *A61K 40/19* (2025.01); *A61K 40/24* (2025.01); *A61K 40/31* (2025.01); *A61K 40/4201* (2025.01); *C07K 14/70539* (2013.01); *C12N 15/86* (2013.01); *C12N 2510/00* (2013.01)

(58) Field of Classification Search

None

See application file for complete search history.

(56) References Cited

U.S. PATENT DOCUMENTS

| | | | |
|---|---|---|---|
| 10,611,816 | B2 | 4/2020 | Tran et al. |
| 2016/0331821 | A1 | 11/2016 | Levey et al. |
| 2019/0002515 | A1 | 1/2019 | Milosevic et al. |

FOREIGN PATENT DOCUMENTS

| | | |
|---|---|---|
| WO | WO 2020/082130 | 4/2020 |

OTHER PUBLICATIONS

Rossjohn et al. (Annu. Rev. Immunol. 2015. 33:169-200).*

Linette et al. (Blood (2013) 122 (6): 863-871).*

Liu et al. (Frontier in Oncology, vol. 11, Jan. 25, 2022).*

Cafri et al., "Memory T cells targeting oncogenic mutations detected in peripheral blood of epithelial cancer patients," *Nat Commun*, 10, 449 (2019).

Cohen et al., Enhanced antitumor activity of murine-human hybrid T-cell receptor (TCR) in human lymphocytes is associated with improved pairing and TCR/CD3 stability, *Cancer Res*, 66, 8878-8886 (2006).

Cohen et al., Enhanced antitumor activity of T cells engineered to express T-cell receptors with a second disulfide bond. *Cancer Res* 67, 3898-3903 (2007).

Haga-Friedman et al., "Incorporation of transmembrane hydrophobic mutations in the TCR enhance its surface expression and T cell functional avidity." *J Immunol*, 188, 5538-5546 (2012).

International Search Report and Written Opinion for Application No. PCT/US2021/060482, mailed Mar. 23, 2022 (18 pages).

Picelli et al.,"Full-length RNA-seq from single cells using Smart-seq2," *Nat Protoc*, 9, 171-181 (2014).

Sidney et al., "Five HLA-DP molecules frequently expressed in the worldwide human population share a common HLA supertypic binding specificity," *J Immunol*, 184, 2492-2503 (2010).

Tran et al., "T-Cell Transfer Therapy Targeting Mutant KRAS in Cancer," *N Engl J Med*, 375, 2255-2262 (2016).

* cited by examiner

*Primary Examiner* — Gary B Nickol

(74) *Attorney, Agent, or Firm* — Klarquist Sparkman, LLP

(57) ABSTRACT

Isolated T cell receptors (TCRs) that specifically recognize a peptide derived from a mutant form of RET (M918T) are described. The TCRs include an alpha chain variable region and a beta chain variable region having the complementarity determining regions (CDRs) of an alpha chain variable region and beta chain variable region of a TCR isolated from a patient with sporadic MTC whose tumor harbored the RET M918T mutation. Cells, such as T cells, expressing the isolated TCRs can be used to treat cancers expressing M918T RET, such as medullary thyroid cancer (MTC).

26 Claims, 12 Drawing Sheets

Specification includes a Sequence Listing.

TCR-ID-1
mTCRb
77.3
Counts
mTCR-β

TCR-ID-2
mTCRb
70.3
Counts
mTCR-β

TCR-ID-2

Autologous B cells

△ RET WT
● RET M918T

% 4-1BB (CD4+mTCRb+)

Peptide concentration (μg/ml)

HLA-DP mismatched APC

TCR-ID-1
TCR-ID-2
□ APC-4
▨ APC-5
% 4-1BB (CD4+mTCR+)
60
40
20
0
Mock
DPB1*04:01
Mock
DPB1*04:01

TCR-ID-1
COS7-DPB1*04:01
% 4-1BB
(CD4+mTCRb+)
0
2
4
6
8
WT
M918T
RET RNA

TCR-ID-2
COS7-DPB1*04:01
% 4-1BB
(CD4+mTCRb+)
0
2
4
6
8
WT
M918T
RET RNA

TCR-ID-1
APC-6
RET WT
RET M918T
%4-1BB (CD4+mTCR+)
50
40
30
20
10
0
10
1
0.1
0.01
Peptide concentration (ug/mL)

TCR-ID-2
APC-6
RET WT
RET M918T
%4-1BB (CD4+mTCR+)
50
40
30
20
10
0
10
1
0.1
0.01
Peptide concentration (ug/mL)

APC-8
RET WT
RET M918T
% 4-1BB (CD4 mTCR+)
30
20
10
0
10
1
0.1
0.01
Peptide concentration (ug/mL)

APC-8
RET WT
RET M918T
% 4-1BB (CD4 mTCR+)
30
20
10
0
10
1
0.1
0.01
Peptide concentration (ug/mL)

Counts
mTCRb
33.2
mTCR-β

% 4-1BB
(CD4+mTCRb+)
80
60
40
20
0
RET WT
RET M918T
10
1
0.1
0.01
0.001
0
Peptide concentration (μg/ml)

% 4-1BB
(CD4+mTCRb+)
60
40
20
0
None
DQ
DR
DP
HLA-II blocking antibody

HLA-DPB1*04:01 APC
APC-1
APC-2
APC-3
% 4-1BB (CD4+mTCRb+)
100
75
50
25
0
WT
M918T
RET Peptide (10 ug/mL)

HLA-DPB1*04:02 APC
APC-4
APC-5
APC-6
% CD137 (CD4+mTCR+)
100
75
50
25
0
WT
M918T
RET Peptide (10 ug/mL)

Mock
DPB1*04:01
%CD137 (CD4+mTCRb+)
20
15
10
5
0
7
8
9
DPB1*04:01-negative APC
MZ-CRC (RET-M918T)
%CD137 (CD4+mTCR+)
15
10
5
0
Mock
DPB1*04:01
HLA construct

T CELL RECEPTORS SPECIFIC FOR A MUTANT FORM OF THE RET ONCOGENE AND USES THEREOF

CROSS-REFERENCE TO RELATED APPLICATIONS

This application is the U.S. National Stage of International Application No. PCT/US2021/060482, filed Nov. 23, 2021, which was published in English under PCT Article 21(2), and which claims the benefit of U.S. Provisional Patent Application No. 63/117,859, filed on Nov. 24, 2020. The above-listed applications are herein incorporated by reference in their entirety.

FIELD

This disclosure concerns isolated T cell receptors (TCRs) that specifically recognize a mutant form of the RET oncogene, and T cells expressing the TCRs. This disclosure further relates to use of the T cells for cancer immunotherapy, such as for the treatment of medullary thyroid cancer.

INCORPORATION OF ELECTRONIC SEQUENCE LISTING

The electronic sequence listing, submitted herewith as a .txt file named 105223-03_ST25.txt (30,641 bytes), created on May 18, 2023, is herein incorporated by reference in its entirety.

BACKGROUND

The RET ("rearranged during transfection") proto-oncogene encodes a receptor tyrosine kinase (RTK) containing extracellular, transmembrane and intracellular tyrosine kinase domains (Itoh et al., *Tumor Res* 24: 1-13, 1998). Ligands for the RET-encoded RTK include neurotropic factors of the glial cell-line derived neurotrophic factor (GDNF) family, such as GDNF, neurturin, artemin and persephin (Jhiang, *Oncogene* 19: 5590-5597, 2000). Gain of function mutations in RET are associated with the development of certain types of cancer, including medullary thyroid cancer (MTC). MTC is a rare endocrine tumor originating from parafollicular C cells of the thyroid (Romei et al., *Oncotarget* 9(11): 9875-9884, 2018). The RET M918T somatic mutation is most frequently found in sporadic forms of MTC (Romei et al., *Nat Rev Endocrinol* 12(4): 192-202, 2016).

SUMMARY

Disclosed herein are isolated or recombinant T cell receptors (TCRs) that specifically recognize a peptide derived from mutant M918T RET, which is expressed on MTC and other types of tumor cells, such as some types of breast cancer and bile duct cancer. The TCRs include an alpha chain variable region and a beta chain variable region having the complementarity determining regions (CDRs) of an alpha chain variable region and beta chain variable region of a TCR isolated from a patient with sporadic MTC whose tumor harbored the RET M918T mutation.

Provided herein are isolated or engineered TCRs having antigenic specificity for M918T RET. In some embodiments, the TCRs include an alpha chain variable region comprising the CDR1, CDR2 and CDR3 sequences of SEQ ID NO: 2, SEQ ID NO: 6 or SEQ ID NO: 19; and a beta chain variable region comprising the CDR1, CDR2 and CDR3 sequences of SEQ ID NO: 4, SEQ ID NO: 8 or SEQ ID NO: 21. In some examples, the TCRs further include an alpha chain constant region and/or a beta chain constant region. The constant regions can be from any species, such as mouse or human. In some examples, the TCRs are HLA-DPA1*01:03, HLA-DPB1*04:01 or HLA-DPB1*04:02 restricted.

Also provided are nucleic acid molecules and vectors that encode the disclosed TCRs, as well as host cells transduced with the nucleic acid molecules and vectors. For example, the host cells can be T cells, such as human T cells. Methods of making a T cell expressing a TCR disclosed herein are also provided.

Further provided are compositions that include a pharmaceutically acceptable carrier and an isolated TCR, nucleic acid molecule, vector or host cell disclosed herein.

Also provided are methods of treating a cancer expressing M918T RET in a subject. In some embodiments, the method includes administering to the subject a therapeutically effective amount of an isolated host cell expressing an M918T RET-specific TCR, as disclosed herein. In some examples, the cancer is MTC.

Methods of making transduced T cells expressing a TCR disclosed herein are further provided. In some embodiments, the method includes obtaining a population of lymphocytes from a subject, contacting the population of lymphocytes with an anti-CD3 antibody and interleukin-2 to produce a population of activated T cells; and transducing the population of activated T cells with a vector disclosed herein.

The foregoing and other objects and features of the disclosure will become more apparent from the following detailed description, which proceeds with reference to the accompanying figures.

BRIEF DESCRIPTION OF THE DRAWINGS

(FIGS. 3A-3B) CRI-2366 autologous peripheral blood T cells transduced to express TCR-ID-1 (FIG. 3A) or TCR-ID-2 (FIG. 3B) were cocultured overnight with autologous B cells pulsed with titrating amounts of the 25 amino acid RET wild type peptide (RET WT; SEQ ID NO: 9) or RET M918T mutated peptide (SEQ ID NO: 10), and flow cytometry was used to detect expression of the T-cell activation marker 4-1BB on transduced mouse TCR-beta (mTCRb) cells. (FIG. 3C) T cells described in FIG. 3A and FIG. 3B were cocultured overnight with HLA-DP-matched, allogeneic PBMC from three different donors (APC-1, -2, -3) that were pulsed with WT or M918T RET peptide (10 μg/mL), and flow cytometry was used to evaluate 4-1BB on the transduced T cells. (FIG. 3D) T cells described in FIG. 3A and FIG. 3B were cocultured with HLA-DP mismatched, allogeneic PBMC from two different donors (APC-4, -5)

that were transfected with water (Mock) or RNA encoding HLA-DPA1*01:03/DPB1*04:01 (hereafter referred to as DPB1*04:01) and pulsed with 10 μg/mL RET M918T mutated peptide. 4-1BB was evaluated as in FIG. 3C. (FIGS. 3E-3F) T cells as described in FIG. 3A and FIG. 3B were cocultured with COS-7 cells transfected with RNA encoding DPB1*04:01 and pulsed with titrating amounts of the RET wild-type or RET M918T peptides, and flow cytometry was used to detect 4-1BB expression on the transduced T cells.

(FIGS. 4A-4B) T cells transduced to express TCR-ID-1 or TCR-ID-2 were cocultured overnight with COS-7 cells co-transfected with RNA encoding HLA-DPB1*04:01 and either RNA encoding wild type (WT) RET or RET M918T, and flow cytometry was used to detect 4-1BB expression on the transduced T cells. (FIGS. 4C-4D) T cells in FIG. 4A and FIG. 4B were cocultured with the medullary cancer cell line MZ-CRC (which endogenously expresses the RET M918T mutation) transfected with water (Mock) or RNA encoding HLA-DPB1*04:01, and flow cytometry was used to detect 4-1BB expression on the transduced T cells.

(FIG. 6A) CRI-2366 autologous peripheral blood T cells were stimulated with anti-CD3 antibody (OKT3) and IL-2 (300 IU/mL) for two days and then transduced with retrovirus encoding TCR-ID-3. Flow cytometry was used to detect expression of the mouse TCR-beta constant region which is engineered into the introduced TCRs. (FIG. 6B) Cells described in FIG. 6A were cocultured overnight with autologous antigen presenting cells (APCs) pulsed with titrating amounts of the 25 amino acid RET wild type peptide (WT) or RET M918T mutated peptide, and flow cytometry was used to detect expression of the T-cell activation marker 4-1BB on transduced mTCRb cells. (FIG. 6C) The T cells described in FIG. 6A were cocultured with autologous APC that were incubated with no antibodies, or blocking antibodies to HLA-DQ (DQ), HLA-DR (DR) or HLA-DP (DP) that were pulsed with RET M918T peptide, and flow cytometry was used to detect the expression of the T-cell activation marker 4-1BB on the transduced T cells the following day. (FIG. 6D) T cells described in FIG. 6A were cocultured overnight with HLA-DP-matched, allogeneic PBMC from three different donors (APC-1, -2, -3) that were pulsed with WT or M918T RET peptide (10 μg/mL), and flow cytometry was used to evaluate 4-1BB on the transduced T cells. (FIG. 6E) Same as FIG. 6D, except the allogeneic donors expressed HLA-DPB1*04:02 rather than HLA-DPB1*04:01. (FIG. 6F) T cells expressing TCR-ID-3 were cocultured with allogeneic PBMC completely mismatched at the HLA-DP locus that were mock-transfected or transfected with RNA encoding HLA-DPA1*01:03/DPB1*04:01 ("DPB1*04:01") and 4-1BB was measured by flow cytometry the following day. (FIG. 6G) T cells expressing TCR-ID-3 were cocultured with the MZ-CRC medullary thyroid cancer cell line that was mock transfected or transfected with RNA encoding HLA-DPB1*04:01 and the next day flow cytometry was used to detect 4-1BB expression on the transduced T cells.

SEQUENCE LISTING

Figure 1:
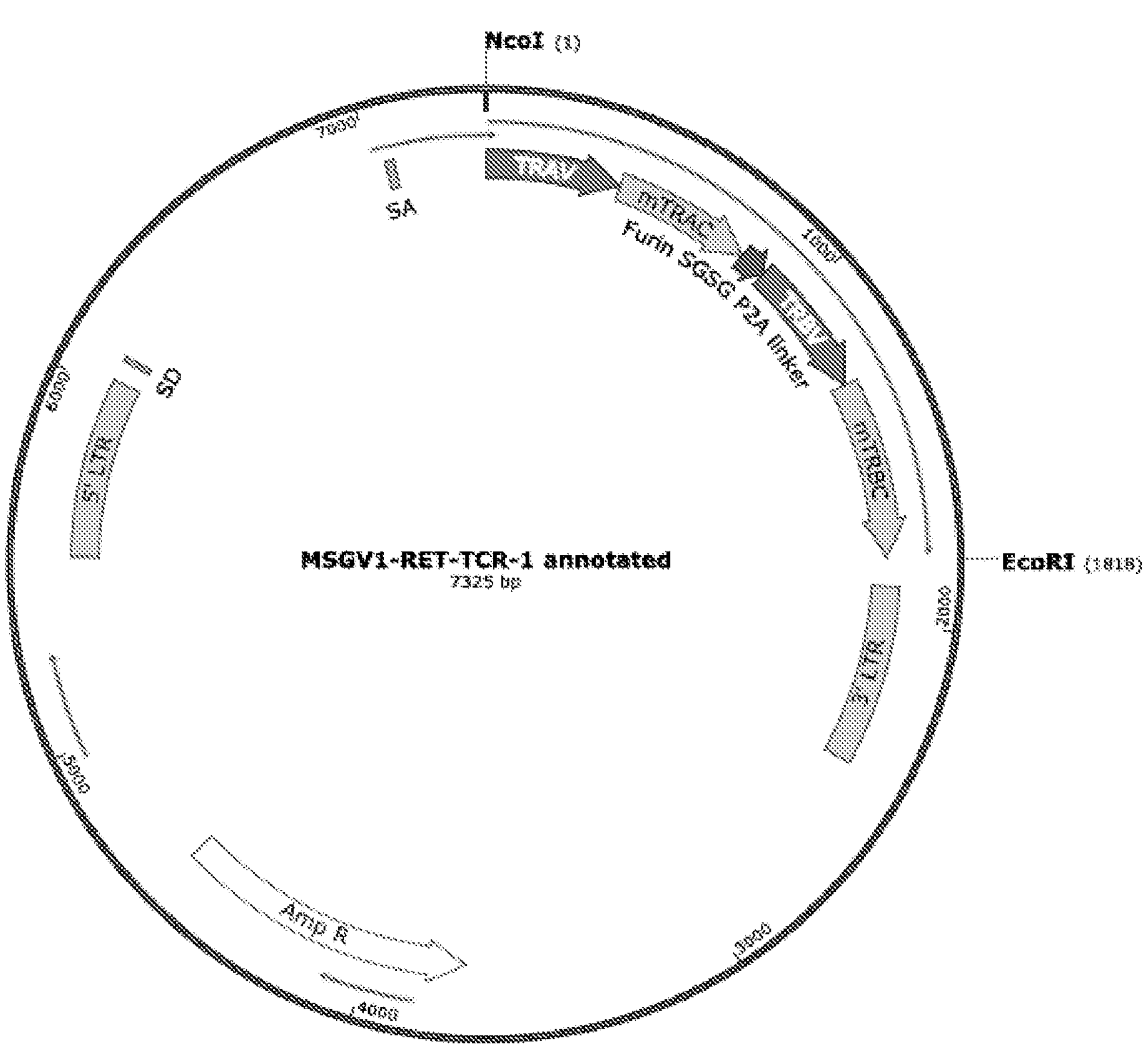
FIG. 1: Schematic of a RET M918T-reactive TCR cloned into the MSGV1 retroviral vector. TRAY, human TCR alpha variable chain; mTRAC, murine TCR-alpha chain constant region; TRBV, human TCR beta variable chain; mTRBC, murine TCR-beta chain constant region.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is a nucleotide sequence encoding TCR alpha chain TRAV9-2*01.

SEQ ID NO: 2 is the amino acid sequence of TCR alpha chain TRAV9-2*01.

SEQ ID NO: 3 is a nucleotide sequence encoding TCR beta chain TRBV6-5*01.

SEQ ID NO: 4 is the amino acid sequence of TCR beta chain TRBV6-5*01.

SEQ ID NO: 5 is a nucleotide sequence encoding TCR alpha chain TRAV14/DV4*02.

SEQ ID NO: 6 is the amino acid sequence of TCR alpha chain TRAV14/DV4*02.

SEQ ID NO: 7 is a nucleotide sequence encoding TCR beta chain TRBV2*01.

SEQ ID NO: 8 is the amino acid sequence of TCR beta chain TRBV2*01.

SEQ ID NO: 9 is the amino acid sequence of the 25-amino acid wild-type RET peptide.

SEQ ID NO: 10 is the amino acid sequence of the 25-amino acid RET M918T mutant peptide.

SEQ ID NO: 11 is the amino acid sequence of wild-type human RET, deposited under GenBank Accession No. NP_066124.1.

SEQ ID NO: 12 is the amino acid sequence of a modified mouse TCR alpha chain constant region.

SEQ ID NO: 13 is the amino acid sequence of a modified mouse TCR beta chain constant region (TCB1).

SEQ ID NO: 14 is the amino acid sequence a mouse TCR beta chain constant region (TCB2).

SEQ ID NO: 15 is the amino acid sequence of a human TCR alpha chain constant region.

SEQ ID NO: 16 is the amino acid sequence of a human TCR beta chain constant region.

SEQ ID NO: 17 is the amino acid sequence of a human TCR beta chain constant region.

SEQ ID NO: 18 is a nucleotide sequence encoding TCR alpha chain TRAV29DV5*01.

SEQ ID NO: 19 is the amino acid sequence of TCR alpha chain TRAV29DV5*01.

SEQ ID NO: 20 is a nucleotide sequence encoding TCR beta chain TRBV7-8*01.

SEQ ID NO: 21 is the amino acid sequence of TCR beta chain TRBV7-8*01.

DETAILED DESCRIPTION

I. Abbreviations

CDR complementarity determining region
CTL cytotoxic T lymphocyte
DC dendritic cell
FACS fluorescence activated cell sorting
GDNF glial cell-line derived neurotrophic factor
HLA human leukocyte antigen MHC major histocompatibility complex
MTC medullary thyroid cancer
mTRAC murine TCR alpha chain constant region
mTRBC murine TCR beta chain constant region
PBMC peripheral blood mononuclear cell
RET rearranged during transfection
RTK receptor tyrosine kinase
TCR T cell receptor
TRAY TCR alpha variable chain
TRBV TCR beta variable chain
WT wild type

II. Terms and Methods

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of a composition, such as a composition comprising cells expressing a TCR disclosed herein, into a subject by a chosen route. Administration can be local or systemic. Exemplary routes of administration include, but are not limited to, oral, injection (such as subcutaneous, intramuscular, intradermal, intraperitoneal, intravenous, and intratumoral, such as intramedullary), sublingual, rectal, transdermal (for example, topical), intranasal, vaginal, and inhalation routes.

Amino acid substitution: The replacement of an amino acid in a polypeptide with one or more different amino acids. The amino acid substitution can be a conservative amino acid substitution or a non-conservative amino acid substitution. In some examples, the amino acid substitution replaces a native amino acid with a cysteine. In some examples, the amino acid substitution replaces a native amino acid with an aliphatic amino acid, such as leucine, isoleucine or valine.

Antigenic specificity: As used herein, a TCR having "antigenic specificity" refers to a TCR that can specifically bind to and immunologically recognize an antigen (such as a mutant M918T form of the RET proto-oncogene), or an epitope thereof, such that binding of the TCR to the antigen, or the epitope thereof, elicits an immune response.

Autologous: Tissues, cells or nucleic acids taken from an individual's own tissues. For example, in an autologous transfer or transplantation of T cells, the donor and recipient are the same person. Autologous (or "autogeneic" or "autogenous") is related to self, or originating within an organism itself.

Codon-optimized: A nucleic acid molecule encoding a protein can be codon-optimized for expression of the protein in a particular organism by including the codon most likely to encode a particular amino acid at each position of the sequence. Codon usage bias is the difference in the frequency of occurrence of synonymous codons (encoding the same amino acid) in coding DNA. A codon is a series of three nucleotides (a triplet) that encodes a specific amino acid residue in a polypeptide chain or for the termination of translation. There are 20 different naturally-occurring amino acids, but 64 different codons (61 codons encoding for amino acids plus 3 stop codons). Thus, there is degeneracy because one amino acid can be encoded by more than one codon. A nucleic acid sequence can be optimized for expression in a particular organism (such as a human) by evaluating the codon usage bias in that organism and selecting the codon most likely to encode a particular amino acid. Multivariate statistical methods, such as correspondence analysis and principal component analysis, are widely used to analyze variations in codon usage. Computer programs are available to implement the statistical analyses related to codon usage, such as Codon W, GCUA, and INCA.

Complementarity determining region (CDR): A region of hypervariable amino acid sequence that defines the binding specificity of a T cell receptor. The alpha and beta chains of a mammalian TCR each have three CDRs, designated CDR1, CDR2 and CDR3.

Conservative variants: "Conservative" amino acid substitutions are those substitutions that do not substantially affect or decrease a function of a protein, such as the ability of the protein to induce an immune response when administered to a subject. In some embodiments, a disclosed polypeptide (such as a TCR alpha variable chain, alpha constant chain, beta variable chain or beta constant chain) includes from 1 to 10 (such as up to 1, up to 2, up to 3, up to 4, up to 5, up to 6, up to 7, up to 8, up to 9, or up to 10) conservative substitutions compared to the corresponding native sequence. The term conservative variation also includes the use of a substituted amino acid in place of an unsubstituted parent amino acid.

Furthermore, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Thus, a conservative substitution does not alter the basic function of a protein of interest. Non-conservative substitutions are those that reduce an activity or function of the protein, such as the ability to induce an immune response when administered to a subject. For instance, if an amino acid residue is essential for a function of the protein, even an otherwise conservative substitution may disrupt that activity.

Contacting: Placement in direct physical association; includes both in solid and liquid form. "Contacting" is often used interchangeably with "exposed." For example, contacting can occur in vitro with one or more TCR-expressing host cells and a biological sample (such as a sample containing cancer cells) in solution.

Degenerate variant: In the context of the present disclosure, a "degenerate variant" refers to a polynucleotide encoding a protein (for example, a TCR or portion thereof) that includes a sequence that is degenerate as a result of the genetic code. There are twenty natural amino acids, most of which are specified by more than one codon. Therefore, all degenerate nucleotide sequences are included as long as the amino acid sequence of the TCR (or portion thereof) encoded by the nucleotide sequence is unchanged.

Epitope: An antigenic determinant. These are particular chemical groups or peptide sequences on a molecule that are antigenic (that elicit a specific immune response). A TCR or antibody specifically binds a particular antigenic epitope on a polypeptide.

Heterologous: Originating from a different genetic source.

Host cells: Cells in which a vector can be propagated and its nucleic acid expressed. The term also includes any progeny of the subject host cell. It is understood that all progeny may not be identical to the parental cell since there may be mutations that occur during replication. However, such progeny are included when the term "host cell" is used. The cell may be prokaryotic or eukaryotic, such as a mammalian cell, yeast cell, insect cell, or bacterial cell. In some embodiments, the cell is a human cell, such as a human T cell.

Isolated: An "isolated" biological component has been substantially separated or purified away from other biological components, such as other biological components in which the component naturally occurs, such as other chromosomal and extrachromosomal DNA, RNA, and proteins. Proteins, peptides, nucleic acids, and cells that have been "isolated" include those purified by standard purification methods. Isolated does not require absolute purity, and can include proteins, peptides, nucleic acids, or cells that are at least 50% pure, such as at least 75%, 80%, 90%, 95%, 98%, 99%, or even 99.9% pure.

Medullary thyroid cancer (MTC): A type of cancer that originates in parafollicular C cells located at the interior of the thyroid. MTC is a rare form of thyroid cancer, making up about 3-4% of all thyroid cancers. Activating mutations of the RET proto-oncogene (such as M918T) have been found in both hereditary and sporadic forms of MTC. Treatments for MTC include, for example, surgery (e.g., thyroidectomy, thyroid lobectomy, lymph node dissection), radiation therapy (e.g., external beam radiotherapy), chemotherapy, thyroid hormone therapy (e.g., Levoxyl, Synthroid), and treatment with protein kinase inhibitors (e.g., Vandetanib, Cabozantinib).

Operably linked: A first nucleic acid is operably linked with a second nucleic acid when the first nucleic acid is placed in a functional relationship with the second nucleic acid. For instance, a promoter is operably linked to a coding sequence if the promoter affects the transcription or expression of the coding sequence. Generally, operably linked nucleic acids are contiguous and, where necessary to join two protein coding regions, the open reading frames are aligned.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, PA, 21st Edition (2005), describes compositions and formulations suitable for pharmaceutical delivery of one or more therapeutic compounds, molecules or agents (e.g., TCR-expressing cells).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor size or metastasis. "Ameliorating" refers to the reduction in the number or severity of signs or symptoms of a disease.

Proto-oncogene: A type of gene that causes normal cells to become cancerous when the gene is mutated. When mutated, the proto-oncogene becomes an oncogene. Proto-oncogenes encode proteins involved in regulating cell growth and differentiation.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids and proteins that have been altered solely by addition, substitution, or deletion of a portion of a natural nucleic acid molecule or protein. In the context of the present disclosure, "recombinant" is used interchangeably with "engineered."

RET (rearranged during transfection): A transmembrane receptor and member of the tyrosine protein kinase family of proteins. Binding of ligands (such as GDNF) to this receptor stimulates receptor dimerization and activation of downstream signaling pathways that play a role in cell differentiation, growth, migration and survival. RET is a proto-oncogene that can undergo oncogenic activation through both cytogenetic rearrangement and activating point mutations. The M918T RET mutation is associated with multiple endocrine neoplasia type 2 (MEN2) and medullary thyroid cancer (MTC).

Sample: In the context of the present disclosure, the sample is any sample that contains or could contain cells. Samples include, for example, fluid samples (that contain or may contain cells, such as a blood sample), cell samples, aspirate samples and/or tissue samples. Specific biological samples include, but are not limited to, biopsy samples (such as tumor biopsy samples), needle aspirates, and tissue sections. In some embodiments, the sample contains cells of the thyroid.

T cell: A white blood cell (lymphocyte) that is an important mediator of the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a $CD8^+$ T cell is a cytotoxic T lymphocyte (CTL). In another embodiment, a $CD8^+$ cell is a suppressor T cell. Activated T cells can be detected by an increase in cell proliferation and/or expression of or secretion of one or more cytokines (such as IL-2, IL-4, IL-6, IFNγ, or TNFα). Activation of CD8+ T cells can also be detected by an increase in cytolytic activity in response to an antigen. In some examples, a T cell is transduced with a heterologous nucleic acid (such as one or more of the nucleic acids or vectors disclosed herein encoding a TCR) or expressing one or more heterologous proteins (such as a recombinant TCR).

T cell receptor (TCR): A heterodimeric protein on the surface of a T cell that binds an antigen (such as an antigen bound to an MHC molecule, for example, on an antigen presenting cell). TCRs include alpha and beta chains, each of which is a transmembrane glycoprotein. Each chain has variable and constant regions with homology to immunoglobulin variable and constant domains, a hinge region, a transmembrane domain, and a cytoplasmic tail. Similar to immunoglobulins, TCR gene segments rearrange during development to produce complete variable domains. The recombinant TCRs disclosed herein are comprised of at least an alpha chain variable region and a beta chain variable region. Similar to immunoglobulins, each variable region of a TCR includes three complementarity determining regions (CDR1, CDR2, and CDR3) that confer antigenic specificity. The TCRs disclosed herein specifically recognize HLA molecules presenting a mutant form of RET (M918T).

Subject: Living multi-cellular vertebrate organisms, a category that includes both human and veterinary subjects, including human and non-human mammals (e.g., mice, rats, rabbits, and non-human primates).

Synthetic: Produced by artificial means in a laboratory, for example a synthetic nucleic acid or protein can be chemically synthesized in a laboratory.

Therapeutically effective amount: A quantity of a specific substance, such as TCR-expressing cell, sufficient to achieve a desired effect, such as an immune response in a subject. For instance, the therapeutically effective amount can be the amount necessary to decrease tumor volume or inhibit tumor metastasis. In some embodiments, a therapeutically effective amount is the amount necessary to decrease tumor volume by at least 10%, at least 20%, at least 50%, at least 75%, at least 80%, at least 90%, at least 95%, or even 100%, for example as compared to tumor volume prior to treatment. In other embodiments, a therapeutically effective amount is the amount necessary to inhibit metastasis by at least 10%, at least 20%, at least 50%, at least 75%, at least 80%, at least 90%, at least 95%, or even 100%, such as compared to metastasis in the absence of treatment.

Transduce: Transferring nucleic acid into a cell, such as transfer of a heterologous nucleic acid into a host cell. As used herein, the term transduce (or transfect or transform) include all techniques by which a nucleic acid is introduced into a cell, including but not limited to transformation with plasmid vectors, infection with viral vectors, and introduction of naked DNA by electroporation, nucleofection, lipofection, or particle gun acceleration. A "heterologous" nucleic acid or protein refers to a nucleic acid or protein originating from a different genetic source. For example, a nucleic acid or protein that is heterologous to a cell originates from an organism or individual other than the cell in which it is expressed. In other examples, a heterologous nucleic acid or protein originates from a cell type other than the cell in which it is expressed.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of an inserted gene or genes. In some non-limiting examples, the vector is a viral vector, such as a retroviral vector.

III. T Cell Receptors Targeting M918T RET

Described herein are isolated or engineered T cell receptors (TCRs) that specifically recognize a peptide derived from mutant M918T RET, which is expressed in certain types of cancer, such as medullary thyroid cancer (MTC). The TCRs include an alpha chain variable region and a beta chain variable region having the complementarity determining regions (CDRs) of an alpha chain variable region and beta chain variable region of a TCR isolated from a patient with sporadic MTC whose tumor harbored the RET M918T mutation.

Provided herein are isolated or engineered TCRs having antigenic specificity for M918T RET. In some embodiments, the TCR includes an alpha chain variable region comprising the sequence of one or more of the CDR1, CDR2 and CDR3 (such as each of CDR1, CDR2 and CDR3) of the alpha chain variable region of TCR-ID-1 (SEQ ID NO: 2), TCR-ID-2 (SEQ ID NO: 6), or TCR-ID-3 (SEQ ID NO: 19). In some embodiments, the TCR includes a beta chain variable region comprising the sequence of one or more of the CDR1, CDR2 and CDR3 (such as each of CDR1, CDR2 and CDR3) of the beta chain variable region of TCR-ID-1 (SEQ ID NO: 4), TCR-ID-2 (SEQ ID NO: 8) or TCR-ID-3 (SEQ ID NO: 21).

In specific embodiments, the TCR includes an alpha chain variable region comprising a CDR1, a CDR2 and a CDR3, wherein the amino acid sequences of the CDR1, CDR2 and CDR3 respectively comprise residues 46-51, 69-75 and 110-120 of SEQ ID NO: 2, residues 47-53, 71-78 and 113-123 of SEQ ID NO: 6, or residues 53-58, 76-82 and 117-129 of SEQ ID NO: 19; and a beta chain variable region comprising a CDR1, a CDR2 and a CDR3, wherein the amino acid sequences of the CDR1, CDR2 and CDR3 respectively comprise residues 46-50, 68-72 and 111-119 of SEQ ID NO: 4, residues 46-49, 67-72 and 111-123 of SEQ ID NO: 8, or residues 46-50, 68-73 and 112-126 of SEQ ID NO: 21.

In some examples of the TCR, the alpha chain variable region CDR1, CDR2 and CDR3 respectively comprise residues 46-51, 69-75 and 110-120 of SEQ ID NO: 2; and the beta chain variable region CDR1, CDR2 and CDR3 respectively comprise residues 46-50, 68-72 and 111-119 of SEQ ID NO: 4. In some examples, the amino acid sequence of the alpha chain variable region is least 85%, at least 90%, at least 95%, at least 96%, at least 97%, at least 98%, or at least 99% identical to SEQ ID NO: 2 and/or the amino acid sequence of the beta chain variable region is at least 85%, at least 90%, at least 95%, at least 96%, at least 97%, at least 98%, or at least 99% identical to SEQ ID NO: 4. In specific non-limiting examples, the amino acid sequence of alpha chain variable region comprises SEQ ID NO: 2 and the amino acid sequence of the beta chain variable region comprises SEQ ID NO: 4.

In other examples of the TCR, the alpha chain variable region CDR1, CDR2 and CDR3 respectively comprise residues 47-53, 71-78 and 113-123 of SEQ ID NO: 6 and the beta chain variable region CDR1, CDR2 and CDR3 respectively comprise residues 46-49, 67-72 and 111-123 of SEQ ID NO: 8. In some examples, the amino acid sequence of the alpha chain variable region is least 85%, at least 90%, at least 95%, at least 96%, at least 97%, at least 98%, or at least 99% identical to SEQ ID NO: 6 and/or the amino acid sequence of the beta chain variable region is at least 85%, at least 90%, at least 95%, at least 96%, at least 97%, at least 98%, or at least 99% identical to SEQ ID NO: 8. In specific non-limiting examples, the amino acid sequence of alpha chain variable region comprises SEQ ID NO: 6 and the amino acid sequence of the beta chain variable region comprises SEQ ID NO: 8.

In other examples of the TCR, the alpha chain variable region CDR1, CDR2 and CDR3 respectively comprise residues 53-58, 76-82 and 117-129 of SEQ ID NO: 19 and the beta chain variable region CDR1, CDR2 and CDR3 respectively comprise residues 46-50, 68-73 and 112-126 of SEQ ID NO: 21. In some examples, the amino acid sequence of the alpha chain variable region is least 85%, at least 90%, at least 95%, at least 96%, at least 97%, at least 98%, or at least 99% identical to SEQ ID NO: 19 and/or the amino acid sequence of the beta chain variable region is at least 85%, at least 90%, at least 95%, at least 96%, at least 97%, at least 98%, or at least 99% identical to SEQ ID NO: 21. In specific non-limiting examples, the amino acid sequence of alpha chain variable region comprises SEQ ID NO: 19 and the amino acid sequence of the beta chain variable region comprises SEQ ID NO: 21.

In some embodiments, the TCR further includes an alpha chain constant region and/or a beta chain constant region. The constant regions can be from any species, such as a heterologous species (e.g., a species other than human). In some examples, the alpha chain constant region is a mouse alpha chain constant region. In specific examples, the mouse alpha chain constant region has an amino acid sequence at least 85%, at least 90%, at least 95%, at least 96%, at least 97%, at least 98%, or at least 99% identical to SEQ ID NO: 12. In particular non-limiting examples, the amino acid sequence of the mouse alpha chain constant region comprises or consists of SEQ ID NO: 12. In some instances, the amino acid at position 1 of SEQ ID NO: 12 is an asparagine. In other examples, the alpha chain constant region is a human alpha chain constant region. In specific examples, the human alpha chain constant region has an amino acid sequence at least 85%, at least 90%, at least 95%, at least 96%, at least 97%, at least 98%, or at least 99% identical to SEQ ID NO: In particular non-limiting examples, the amino acid sequence of human alpha chain constant region comprises or consists of SEQ ID NO: 15. In some instances, the amino acid at position 1 of SEQ ID NO: 15 is an asparagine.

In some examples, the beta chain constant region is a mouse beta chain constant region. In specific examples, the mouse beta chain constant region has an amino acid sequence at least 85%, at least 90%, at least 95%, at least 96%, at least 97%, at least 98%, or at least 99% identical to SEQ ID NO: 13 (TCB1) or SEQ ID NO: 14 (TCB2). In particular non-limiting examples, the amino acid sequence of the mouse beta chain constant region comprises or consists of SEQ ID NO: 13 or SEQ ID NO: 14. In other examples, the beta chain constant region is a human beta chain region. In specific examples, the human beta chain constant region has an amino acid sequence at least 85%, at least 90%, at least 95%, at least 96%, at least 97%, at least 98%, or at least 99% identical to SEQ ID NO: 16 or SEQ ID NO: 17. In particular non-limiting examples, the amino acid sequence of the human beta chain constant region comprises or consists of SEQ ID NO: 16 or SEQ ID NO: 17.

In some examples, the TCRs are HLA-DPA1*01:03, HLA-DPB1*04:01 or HLA-DPB1*04:02 restricted.

Also provided herein are nucleic acid molecules encoding a disclosed M918T RET-specific TCR.

In some embodiments, the nucleic acid molecule has a nucleotide sequence at least 85%, at least 90%, at least 95%, at least 96%, at least 97%, at least 98%, or at least 99% identical to SEQ ID NO: 1 (or degenerate variant thereof), SEQ ID NO: 3 (or degenerate variant thereof) or SEQ ID NO: 18 (or degenerate variant thereof). In some examples, the nucleic acid molecule has a nucleotide sequence comprising or consisting of SEQ ID NO: 1, SEQ ID NO: 3 or SEQ ID NO: 18, or a degenerate variant of SEQ ID NO: 1, SEQ ID NO: 3 or SEQ ID NO: 18.

In some embodiments, the nucleic acid molecule has a nucleotide sequence at least 85%, at least 90%, at least 95%, at least 96%, at least 97%, at least 98%, or at least 99% identical to SEQ ID NO: 5 (or a degenerate variant thereof), SEQ ID NO: 7 (or a degenerate variant thereof) or SEQ ID NO: 21 (or a degenerate variant thereof). In some examples, the nucleic acid molecule has a nucleotide sequence comprising or consisting of SEQ ID NO: 5, SEQ ID NO: 7 or SEQ ID NO: 21, or a degenerate variant of SEQ ID NO: 5, SEQ ID NO: 7 or SEQ ID NO: 21.

In specific examples, the nucleic acid molecule comprises SEQ ID NO: 1 and SEQ ID NO: 3; SEQ ID NO: 5 and SEQ ID NO: 7; or SEQ ID NO: 19 and SEQ ID NO: 21.

In some examples, the nucleic acid molecule further includes a heterologous sequence, such as a heterologous promoter.

Further provided herein are isolated nucleic acid molecules encoding a TCR alpha chain variable region and a TCR beta chain variable region.

In some embodiments of the nucleic acid molecules, the encoded alpha chain variable region has an amino acid sequence at least 85%, at least 90%, at least 95%, at least 96%, at least 97%, at least 98%, or at least 99% identical to SEQ ID NO: 2 and/or the encoded beta chain variable region has an amino acid sequence at least 85%, at least 90%, at least 95%, at least 96%, at least 97%, at least 98%, or at least 99% identical to SEQ ID NO: 4. In some examples, the encoded amino acid sequence of the alpha chain variable region comprises or consists of SEQ ID NO: 2 and the encoded amino acid sequence of the beta chain variable region comprises or consists of SEQ ID NO: 4. In specific examples, the isolated nucleic acid molecule comprises or consists of the nucleotide sequences of SEQ ID NO: 1 and SEQ ID NO: 3, or degenerate variants thereof.

In other embodiments, the encoded alpha chain variable region has an amino acid sequence at least 85%, at least 90%, at least 95%, at least 96%, at least 97%, at least 98%, or at least 99% identical to SEQ ID NO: 6 and/or the encoded beta chain variable region has an amino acid sequence at least 85%, at least 90%, at least 95%, at least 96%, at least 97%, at least 98%, or at least 99% identical to SEQ ID NO: 8. In some examples, the encoded amino acid sequence of the alpha chain variable region comprises or consist of SEQ ID NO: 6 and the encoded amino acid sequence of the beta chain variable region comprises or consists of SEQ ID NO: 8. In specific examples, the isolated nucleic acid molecule comprises or consists of the nucleotide sequences of SEQ ID NO: 5 and SEQ ID NO: 7, or degenerate variants thereof.

In other embodiments, the encoded alpha chain variable region has an amino acid sequence at least 85%, at least 90%, at least 95%, at least 96%, at least 97%, at least 98%, or at least 99% identical to SEQ ID NO: 19 and/or the encoded beta chain variable region has an amino acid sequence at least 85%, at least 90%, at least 95%, at least 96%, at least 97%, at least 98%, or at least 99% identical to SEQ ID NO: 21. In some examples, the encoded amino acid sequence of the alpha chain variable region comprises or consist of SEQ ID NO: 19 and the encoded amino acid sequence of the beta chain variable region comprises or consists of SEQ ID NO: 21. In specific examples, the isolated nucleic acid molecule comprises or consists of the nucleotide sequences of SEQ ID NO: 18 and SEQ ID NO: 20, or degenerate variants thereof.

In some embodiments, the nucleic acid molecule further includes a heterologous sequence, such as a heterologous promoter or a heterologous vector sequence.

In some embodiments, the isolated nucleic acid molecule encoding a TCR alpha chain variable region and a TCR beta chain variable region further includes a nucleotide sequence encoding an alpha chain constant region and/or a nucleotide sequence encoding a beta chain constant region. The alpha and beta constant regions can be from any species.

In some examples, the alpha chain constant region is a murine alpha chain constant region, for example the nucleic acid encodes an alpha chain constant region having an amino acid sequence at least 85%, at least 90%, at least 95%, at least 96%, at least 97%, at least 98%, or at least 99% identical to SEQ ID NO: 12. In specific examples, the encoded amino acid sequence of the murine alpha chain constant region comprises of consists of SEQ ID NO: 12. In some examples, the encoded beta chain constant region is a murine beta chain constant region, for example a murine beta chain constant region having an amino acid sequence at least 85%, at least 90%, at least 95%, at least 96%, at least 97%, at least 98%, or at least 99% identical to of SEQ ID NO: 13 or SEQ ID NO: 14. In specific examples, the encoded amino acid sequence of the murine beta chain constant region comprises or consists of SEQ ID NO: 13 or SEQ ID NO: 14. In some examples, the nucleotide sequence encoding the murine alpha chain constant region and/or the nucleotide sequence encoding the murine beta chain constant region is/are codon-optimized for expression in mammalian cells, such as human cells.

In other examples, the encoded alpha chain constant region is a human alpha chain constant region, for example a human alpha chain constant region having an amino acid sequence at least 85%, at least 90%, at least 95%, at least 96%, at least 97%, at least 98%, or at least 99% identical to SEQ ID NO: 15. In some examples, the encoded amino acid sequence of the human alpha chain constant region comprises or consists of SEQ ID NO: 15. In some instances, the amino acid encoded at position 1 of SEQ ID NO: 15 is an asparagine. In some examples, the encoded beta chain constant region is a human beta chain constant region, for example a human beta chain constant region having an amino acid sequence at least 85%, at least 90%, at least 95%, at least 96%, at least 97%, at least 98%, or at least 99% identical to SEQ ID NO: 16 or SEQ ID NO: 17. In some examples, the encoded amino acid sequence of the human beta chain constant region comprises or consists of SEQ ID NO: 16 or SEQ ID NO: 17.

In some embodiments, the isolated nucleic acid molecule further includes a nucleotide sequence encoding a self-cleaving peptide sequence. In some examples, the self-cleaving peptide is a 2A peptide, such as a 2A peptide from porcine teschovirus-1 (P2A), Thosea asigna virus (T2A), foot and mouth disease virus (F2A) or equine rhinitis A virus (E2A), or a variant thereof. In specific examples, the 2A peptide is P2A.

In some embodiments, the isolated nucleic acid molecule comprises in the 5' to 3' direction: an alpha chain variable region, an alpha chain constant region, a self-cleaving peptide sequence (such as a 2A peptide linker sequence), a beta chain variable region and a beta chain constant region, as disclosed herein.

In some embodiments, the isolated nucleotide acid molecule is operably linked to a promoter, for example a heterologous promoter.

Further provided herein are vectors that contain a nucleic acid molecule disclosed herein. The vector can be any vector suitable for expression of a nucleic acid molecule encoding a TCR or portion thereof (such as an alpha chain variable region and/or a beta chain variable region). In some embodiments, the vector is a viral vector, such as a retroviral vector, for example a murine stem cell virus (MSCV)-based splice-gag (MSGV1) vector. Additional viral vectors suitable for nucleic acid delivery to T cells include lentivirus, adenovirus, adeno-associated virus, vaccinia virus, alphavirus, herpesvirus, and fowlpox virus vectors. In other embodiments, the vector is a plasmid vector. One of ordinary skill in the art can select an appropriate vector, for example to stably or transiently transduce host cells (such as T cells) with the TCRs described herein.

Also provided are isolated host cells that include a nucleic acid molecule or vector disclosed herein. In some embodiments, the cell is a prokaryotic cell, such as a bacterial cell (for example, *E. coli*). In other embodiments, the cell is a eukaryotic cell, such as a mammalian cell. In some examples, the mammalian cell is a human cell, such as a human immune cell, for example a T cell. Methods of introducing a vector into a host cell are known to one of ordinary skill in the art and include, for example, transformation (e.g. with plasmid vectors), infection (e.g., with viral vectors), and electroporation, nucleofection, lipofection, or particle gun acceleration (e.g., naked DNA).

Further provided herein are compositions that include a pharmaceutically acceptable carrier and an isolated TCR, nucleic acid molecule, vector, or isolated host cell disclosed herein.

Also provided are methods of treating a cancer expressing M918T RET in a subject. In some embodiments, the method includes administering to the subject a therapeutically effective amount of an isolated host cell disclosed herein. In some examples the cancer is medullary thyroid cancer. Methods of treatment are described in more detail in section IV.

Further provided are methods of making transduced T cells expressing a TCR disclosed herein. In some embodiments, the method includes obtaining a population of lymphocytes from a subject; contacting the population of lymphocytes with an anti-CD3 antibody and interleukin-2 to produce a population of activated T cells; and transducing the population of activated T cells with a vector disclosed herein, thereby producing the transduced T cells. In some examples, the method further includes expanding the population of transduced T cells. In particular examples, the lymphocytes are obtained from a subject with medullary thyroid cancer. Other methods for producing T cells (or other cells) expressing a disclosed TCR are known in the art and can be used to produce cells expressing a disclosed TCR (for example, CRISPR/Cas9 and transposon/transposase systems).

IV. Compositions and Methods for Treating Cancer

Disclosed herein are methods of treating or inhibiting a cancer expressing M918T RET in a subject by administering to the subject a host cell, such as a T cell, a natural killer cell, NKT cell or gamma delta T cell (or a population of T cells, NK cells NKT cells or gamma delta T cells) expressing a TCR (such as an alpha chain variable region and a beta chain variable region) disclosed herein. In some non-limiting examples, the cancer is medullary thyroid cancer, breast cancer or bile duct cancer. In other examples, the cancer expressing M918T RET is an adrenal cancer or a cancer of the meninges.

Compositions are provided that include the TCRs disclosed herein, e.g., nucleic acids encoding the TCRs and/or TCR-expressing cells, in combination with one or more pharmaceutically or physiologically acceptable carriers, diluents or excipients. A "pharmaceutically acceptable carrier" includes any and all solvents, dispersion media, coatings, antibacterial and antifungal agents, isotonic and absorption delaying agents, and the like, compatible with pharmaceutical administration. Examples of such carriers or diluents include, but are not limited to, water, saline, Ringer's solutions, dextrose solution, 5% human serum albumin; buffers (such as neutral buffered saline, phosphate buffered saline and the like); carbohydrates such as glucose, mannose, sucrose, dextrans, or mannitol; proteins; polypeptides or amino acids such as glycine; antioxidants; chelating agents such as EDTA or glutathione; adjuvants (e.g., aluminum hydroxide); and preservatives. Liposomes and non-aqueous vehicles such as fixed oils may also be used. Supplementary active compounds can also be incorporated into the compositions. Actual methods for preparing administrable compositions are known or apparent to those skilled in the art and are described in more detail in such publications as *Remington: The Science and Practice of Pharmacy*, The University of the Sciences in Philadelphia, Editor, Lippincott, Williams, & Wilkins, Philadelphia, PA, $21^{st}$ Edition (2005).

With regard to the cells, a variety of aqueous carriers can be used, for example, buffered saline and the like, for introducing the cells. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration in these formulations can vary widely, and will be selected primarily based on fluid volumes, viscosities, body weight and the like in accordance with the particular mode of administration selected and the subject's needs.

The precise amount of the composition to be administered can be determined by a physician with consideration of individual differences in age, weight, tumor size, extent of metastasis, and condition of the patient (subject). In some examples, the composition includes about $10^4$ to $10^{12}$ of the TCR-expressing host cells (for example, about $10^4$-$10^7$ cells, about $10^6$-$10^9$ cells, or about $10^8$-$10^{12}$ cells). For example, the composition may be administered at a dose of about $10^4$ to $10^9$ cells/kg body weight, such as $10^5$ to $10^6$ cells/kg body weight, including all integer values within those ranges. Exemplary doses are $10^6$ cells/kg to about $10^8$ cells/kg, such as from about $5\times10^6$ cells/kg to about $7.5\times10^7$ cells/kg, such as at about $2.5\times10^7$ cells/kg, or at about $5.0\times10^7$ cells/kg.

The disclosed composition can be administered once or multiple times, such as 2, 3, 4, 5, 6, 7, 8, 9 or 10 times at these dosages. The compositions can be administered daily, weekly, bimonthly or monthly. In some non-limiting examples, the composition is formulated for intravenous administration and is administered multiple times. The quantity and frequency of administration will be determined by such factors as the condition of the subject, and the type and severity of the subject's disease, although appropriate dosages may be determined by clinical trials.

The administration of the compositions may be carried out in any convenient manner, including by injection, transfusion, implantation or transplantation. The disclosed compositions can be administered to a patient trans-arterially, subcutaneously, intradermally, intratumorally, intranodally, intramedullary, intramuscularly, by intravenous (i.v.) injection, or intraperitoneally. For example, the composition can be administered using infusion techniques known in immunotherapy (see, e.g., Rosenberg et al., *New Eng. J. of Med.* 319:1676, 1988).

In vivo treatment of a subject is initiated by administration of the TCR-expressing host cells disclosed herein. The cells can be autologous to the recipient. However, the cells can also be heterologous (allogeneic). Administration is typically via intravenous or intraperitoneal infusion, although direct injection into solid tumors or other such focal lesions can also be used. The efficacy of the treatment can be assessed, for example, by reduction in tumor size and or metastasis. Tumor size and number can be evaluated by imaging (such as MRI, PET, and/or CT imaging) In some examples, staging is done every month, every 3 months, or every 6 months.

In some examples, the disclosed methods decrease the size, volume and/or weight of a tumor by at least 10%, at least 20%, at least 30%, at least 50%, at least 50%, at least 75%, at least 90%, at least 95%, at least 98%, at least 99% or 100%, for example relative to the size, volume and/or weight of the tumor prior to treatment. In some examples, the methods decrease the size, volume and/or weight of a metastasis by at least 10%, at least 20%, at least 30%, at least 50%, at least 50%, at least 75%, at least 90%, at least 95%, at least 98%, at least 99% or 100%, for example relative to the size, volume and/or weight of the metastasis prior to treatment. In some examples, the methods increase the survival time of a subject with a M918T RET-expressing cancer by at least 3 months, at least 6 months, at least 9 months, at least 12 months, at least 18 months, at least 24 months, at last 36 months, at least 48 months, or at least 60 months, for example relative to the survival time in the absence of the treatment provided herein. In some examples, combinations of these effects are achieved.

In some embodiments, the subject has MTC. Methods of identifying a subject with MTC are known to one of ordinary skill in the art and include blood test, radiographic evidence of MTC (for example, imaging by ultrasound, MRI, CT scan, or PET scan) and/or a biopsy (such as a fine needle aspirate or needle core biopsy) confirming the presence of MTC. In some examples, the subject has metastatic MTC. In additional examples, the subject with MTC expresses HLA-DPA1*01:03, HLA-DPB1*04:01 and/or HLA-DPB1*04:02. In other embodiments, the subject has breast cancer or bile duct cancer.

In particular embodiments, the methods include obtaining a population of cells including lymphocytes from a subject with MTC. In other examples, a population of cells including lymphocytes are obtained from an HLA-matched donor to the subject to be treated.

A population of cells including lymphocytes (such as PBMCs) can be obtained by any method, including, but not limited to apheresis. All or a portion of the population of cells can be utilized immediately or all or a portion of the cells can be cryopreserved for future use. When ready for use, all or a portion of the population of cells is thawed (if previously cryopreserved) and T cells are activated by incubation with an anti-CD3 antibody (such as OKT3). In some examples, about $10^7$-$10^9$ PBMCs are incubated with an anti-CD3 monoclonal antibody (e.g., about 30 ng/ml) and optionally also IL-2 (e.g., about 300 IU/ml) and/or IL-15 (about 10-100 ng/ml). In specific examples, about $1\times10^7$ to about $1\times10^8$ PBMCs are incubated with anti-CD3 antibody OKT3 and IL-2 for about 1-5 days (such as about 1 day, about 2 days, about 3 days, about 4 days, or about 5 days).

In some examples, following T cell activation, the cells are enriched for $CD4^+$ cells. Following T cell activation (and optional $CD4^+$ cell enrichment) the cells are transduced with a vector including a heterologous nucleic acid encoding an M918T RET-specific TCR disclosed herein. In particular examples, about $10^7$-$10^9$ cells are transduced (for example, about $1\times10^7$, $2\times10^7$, $3\times10^7$, $4\times10^7$, $5\times10^7$, $1\times10^8$, $5\times10^8$, or $1\times10^9$ cells). In one non-limiting example, about $1\times10^7$ to about $4\times10^7$ cells are transduced.

Transduced T cells are expanded ex vivo and can be cryopreserved at appropriate dosage amounts (for example, about $10^6$ to $10^{12}$ cells) following expansion. In one specific example, the transduced T cells are expanded on irradiated allogeneic PBMC feeder cells (1 billion feeder cells per 10,000,000 T cells) in medium containing 3000 IU/ml IL-2 and 30 ng/ml anti-CD3 (OKT3). The expansion can be for a sufficient time to obtain the desired number of T cells, for example, about 4-14 days (such as 4-9 days, 7-10 days, 8-12 days, 9-14 days, or 9-11 days). In some examples, the T cells are supplemented with fresh IL-2 on days 4, 7, and 11. In some non-limiting examples, the expansion can optionally be carried out in a WAVE bioreactor (GE Healthcare Life Sciences, Pittsburgh, PA) or G-Rex flasks for at least a portion of the expansion, such as for 1-5 days, for example from days 9-14 of the expansion protocol. One of ordinary skill in the art can identify other methods for expanding T cells ex vivo, which can also be used with the transduced T cells described herein (see, e.g., U.S. Pat. No. 5,827,642 and Riddell and Greenberg, *J. Immunol. Meth.* 128:189-201, 1990, incorporated herein by reference in their entirety).

The TCR-expressing cells are thawed (if previously frozen), prior to administration to the subject. The subject may undergo an immunosuppressive regimen (e.g., lymphodepletion) prior to administering the TCR-expressing cells. In one example, the subject is administered cyclophosphamide and/or fludarabine prior to administering the modified T cells. In one non-limiting example, the subject is administered cyclophosphamide (e.g., 60 mg/kg) on days −5 and −4 and/or fludarabine (e.g., 25 mg/m$^2$) on days −5 through −1 (where day 0 is administration of the TCR-expressing cells). In another non-limiting example, the subject is administered cyclophosphamide (1,000 mg/m$^2$ IV) on day −5 and fludarabine (30 mg/m$^2$) on days −5 through −3 (where day 0 is administration of the modified T cells). The TCR-expressing cells are administered to the subject, for example by infusion. In some examples, the TCR-expressing cells are administered at a dose of about $10^4$ to $10^{12}$ cells (for example, about $10^4$-$10^7$ cells, about $10^6$-$10^9$ cells, or about $10^8$-$10^{12}$ cells or about $1\times10^6$ to $1\times10^9$ cells/kg (such as about $1\times10^6$, $5\times10^6$, $1\times10^7$, $5\times10^7$, $1\times10^8$, $5\times10^8$, or $1\times10^9$ cells/kg) Immune system supportive therapies may also be administered to the subject, for example to promote expansion of the TCR-expressing cells in the subject and/or to support recovery of neutrophils. In one non-limiting example, the subject is administered IL-2 (e.g., 600,000 IU/kg or 720,000 IU/kg) for 3 days (or a lower dose of IL-2 for a longer period of time, such as 10 days) and/or G-CSF (e.g., 300-480 μg sc) daily from day +1 until absolute neutrophil count is greater than 500. In another example, the immune system supportive therapy includes administering $2\times10^6$ IU/m$^2$ IL-2 and/or G-CSF every 12 hours for seven days following administration of the TCR-expressing cells.

The subject can also be administered one or more additional treatments or anti-cancer agents before, concurrently, or after treatment with the TCR-expressing cells. The one or more additional treatments can include, for example, surgery (e.g., thyroidectomy, thyroid lobectomy, lymph node dissection), radiation therapy (e.g., external beam radiotherapy), chemotherapy, thyroid hormone therapy (e.g., Levoxyl, Synthroid), and treatment with protein kinase inhibitors (e.g., Vandetanib, Cabozantinib).

In some embodiments, the subject is administered any suitable anti-cancer agent in combination with the TCR-expressing cells disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g., anti-androgens) and anti-angiogenesis agents. Other anti-cancer treatments include radiation therapy and antibodies (e.g., mAbs) that specifically target cancer cells or other cells (e.g., anti-PD-1, anti-CLTA4, anti-EGFR, or anti-VEGF). In one example, a cancer is treated by administering TCR-expressing cells disclosed herein and one or more therapeutic mAbs, such as one or more of a 1 antibody (e.g., durvalumab, KN035, cosibelimab, BMS-936559, BMS935559, MEDI-4736, MPDL-3280A, or MEDI-4737), or CLTA-4 antibody (e.g., ipilimumab or tremelimumab). In one example, a cancer is treated by administering a TCR-expressing cell disclosed herein and one or more mAbs, for example: 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, Tacatuzumab tetraxetan, Taplitumomab paptox, Tenatumomab, TGN1412, Ticilimumab (tremelimumab), Tigatuzumab, TNX-650, Trastuzumab, Tremelimumab, Tucotuzumab celmoleukin, Veltuzumab, Volociximab, Votumumab, Zalutumumab, or combinations thereof.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Exemplary chemotherapy drugs that can be used in combination with the compositions and methods provided herein include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

V. Exemplary Embodiments

Embodiment 1. An isolated T cell receptor (TCR) having antigenic specificity for a mutant form of the rearranged during transfection (RET) proto-oncogene with a methionine to threonine substitution at position 918 of SEQ ID NO: 11, wherein the TCR comprises:

- (a) an alpha chain variable region comprising a complementarity determining region 1 (CDR1), a CDR2 and a CDR3, wherein the amino acid sequences of the CDR1, CDR2 and CDR3 respectively comprise:
  - (i) residues 46-51, 69-75 and 110-120 of SEQ ID NO: 2;
  - (ii) residues 47-53, 71-78 and 113-123 of SEQ ID NO: 6; or
  - (iii) residues 53-58, 76-82 and 117-129 of SEQ ID NO: 19; and
- (b) a beta chain variable region comprising a CDR1, a CDR2 and a CDR3, wherein the amino acid sequences of the CDR1, CDR2 and CDR3 respectively comprise:
  - (i) residues 46-50, 68-72 and 111-119 of SEQ ID NO: 4;
  - (ii) residues 46-49, 67-72 and 111-123 of SEQ ID NO: 8; or
  - (iii) residues 46-50, 68-73 and 112-126 of SEQ ID NO: 21.

Embodiment 2. The isolated TCR of embodiment 1, wherein:

- the alpha chain variable region CDR1, CDR2 and CDR3 respectively comprise residues 46-51, 69-75 and 110-120 of SEQ ID NO: 2; and
- the beta chain variable region CDR1, CDR2 and CDR3 respectively comprise residues 46-50, 68-72 and 111-119 of SEQ ID NO: 4.

Embodiment 3. The isolated TCR of embodiment 1 or embodiment 2, wherein:

- the amino acid sequence of alpha chain variable region comprises SEQ ID NO: 2; and
- the amino acid sequence of the beta chain variable region comprises SEQ ID NO: 4.

Embodiment 4. The isolated TCR of embodiment 1, wherein:

- the alpha chain variable region CDR1, CDR2 and CDR3 respectively comprise residues 47-53, 71-78 and 113-123 of SEQ ID NO: 6; and
- the beta chain variable region CDR1, CDR2 and CDR3 respectively comprise residues 46-49, 67-72 and 111-123 of SEQ ID NO: 8.

Embodiment 5. The isolated TCR of embodiment 1 or embodiment 4, wherein:

- the amino acid sequence of alpha chain variable region comprises SEQ ID NO: 6; and
- the amino acid sequence of the beta chain variable region comprises SEQ ID NO: 8.

Embodiment 6. The isolated TCR of embodiment 1, wherein:

- the alpha chain variable region CDR1, CDR2 and CDR3 respectively comprise residues 53-58, 76-82 and 117-129 of SEQ ID NO: 19; and
- the beta chain variable region CDR1, CDR2 and CDR3 respectively comprise residues 46-50, 68-73 and 112-126 of SEQ ID NO: 21.

Embodiment 7. The isolated TCR of embodiment 1 or embodiment 6, wherein:

- the amino acid sequence of alpha chain variable region comprises SEQ ID NO: 19; and
- the amino acid sequence of the beta chain variable region comprises SEQ ID NO: 21.

Embodiment 8. The isolated TCR of any one of embodiments 1-7, further comprising an alpha chain constant region and/or a beta chain constant region.

Embodiment 9. The isolated TCR of embodiment 8, wherein the alpha chain constant region is a murine alpha chain constant region or a human alpha chain constant region.

Embodiment 10. The isolated TCR of embodiment 9, wherein the alpha chain constant region is a murine alpha chain constant region comprising an amino acid sequence at least 90% identical to SEQ ID NO: 12.

Embodiment 11. The isolated TCR of embodiment 10, wherein the amino acid sequence of the murine alpha chain constant region comprises or consists of SEQ ID NO: 12, wherein the amino acid at position 1 is asparagine.

Embodiment 12. The isolated TCR of any one of embodiments 8-11, wherein the beta chain constant region is a murine beta chain constant region or a human beta chain constant region.

Embodiment 13. The isolated TCR of embodiment 12, wherein the beta chain constant region is a murine beta chain constant region comprising an amino acid sequence at least 90% identical to SEQ ID NO: 13 or SEQ ID NO: 14.

Embodiment 14. The isolated TCR of embodiment 13, wherein the amino acid sequence of the murine beta chain constant region comprises or consists of SEQ ID NO: 13 or SEQ ID NO: 14.

Embodiment 15. An isolated nucleic acid molecule encoding the TCR of any one of embodiments 1-14.

Embodiment 16. The isolated nucleic acid molecule of embodiment 15, wherein:

- the nucleic acid molecule comprises the nucleotide sequence of SEQ ID NO: 1 and SEQ ID NO: 3, or degenerate variants thereof;
- the nucleic acid molecule comprises the nucleotide sequence of SEQ ID NO: 5 and SEQ ID NO: 7, or degenerate variants thereof; or
- the nucleic acid molecule comprises the nucleotide sequence of SEQ ID NO: 18 and SEQ ID NO: 20, or degenerate variants thereof.

Embodiment 17. An isolated nucleic acid molecule encoding a T cell receptor (TCR) alpha chain variable region and a TCR beta chain variable region, wherein:

- the amino acid sequence of the alpha chain variable region comprises SEQ ID NO: 2 and the amino acid sequence of the beta chain variable region comprises SEQ ID NO: 4;
- the amino acid sequence of the alpha chain variable region comprises SEQ ID NO: 6 and the amino acid sequence of the beta chain variable region comprises SEQ ID NO: 8; or
- the amino acid sequence of the alpha chain variable region comprises SEQ ID NO: 19 and the amino acid sequence of the beta chain variable region comprises SEQ ID NO: 21.

Embodiment 18. The isolated nucleic acid molecule of embodiment 17, comprising:

- the nucleotide sequence of SEQ ID NO: 1 and SEQ ID NO: 3, or degenerate variants thereof;
- the nucleotide sequence of SEQ ID NO: 5 and SEQ ID NO: 7, or degenerate variants thereof; or
- the nucleotide sequence of SEQ ID NO: 18 and SEQ ID NO: 20, or degenerate variants thereof.

Embodiment 19. The isolated nucleic acid molecule of embodiment 17 and embodiment 18, further comprising a nucleotide sequence encoding an alpha chain constant region and/or a nucleotide sequence encoding a beta chain constant region.

Embodiment 20. The isolated nucleic acid molecule of embodiment 19, wherein the alpha chain constant region and/or the beta chain constant region are murine constant regions.

Embodiment 21. The isolated nucleic acid molecule of embodiment 20, wherein the alpha chain constant region is a murine alpha chain constant region comprising the amino acid sequence of SEQ ID NO: 12.

Embodiment 22. The isolated nucleic acid molecule of embodiment 20 or embodiment 21, wherein the beta chain constant region is a murine beta chain constant region comprising the amino acid sequence of SEQ ID NO: 13 or SEQ ID NO: 14.

Embodiment 23. The isolated nucleic acid molecule of any one of embodiments 20-22, wherein the nucleotide sequence encoding the murine alpha chain constant region and/or the nucleotide sequence encoding the murine beta chain constant region is/are codon-optimized for expression in mammalian cells.

Embodiment 24. The isolated nucleic acid molecule of any one of embodiments 17-23, further comprising a nucleotide sequence encoding a P2A linker sequence.

Embodiment 25. The isolated nucleic acid molecule of embodiment 24, comprising in the 5' to 3' direction:

- the alpha chain variable region, the alpha chain constant region, the P2A linker sequence, the beta chain variable region and the beta chain constant region; or
- the beta chain variable region, the beta chain constant region, the P2A linker sequence, the alpha chain variable region and the alpha chain constant region.

Embodiment 26. The nucleic acid molecule of any one of embodiments 15-25 operably linked to a promoter.

Embodiment 27. A vector comprising the nucleic acid molecule of any one of embodiments 15-26.

Embodiment 28. The vector of embodiment 27, which is a viral vector.

Embodiment 29. The vector of embodiment 28, wherein the viral vector is a retroviral vector.

Embodiment 30. The vector of embodiment 27, which is a plasmid vector.

Embodiment 31. An isolated host cell comprising the nucleic acid molecule or vector of any one of embodiments 15-30.

Embodiment 32. The isolated host cell of embodiment 31, which is a eukaryotic cell.

Embodiment 33. The isolated host cell of embodiment 32, wherein the eukaryotic cell is a human cell.

Embodiment 34. The isolated host cell of embodiment 33, wherein the human cell is a human T cell.

Embodiment 35. A composition comprising a pharmaceutically acceptable carrier and the isolated TCR of any one of embodiments 1-14, the nucleic acid molecule of any one of embodiments 15-26, the vector of any one of embodiments 27-30, or the isolated host cell of any one of embodiments 31-34.

Embodiment 36. A method of treating a cancer expressing M918T RET in a subject, comprising administering to the subject a therapeutically effective amount of the isolated host cell of any one of embodiments 31-34 or the composition of embodiment 35.

Embodiment 37. The method of embodiment 36, wherein the cancer is medullary thyroid cancer.

Embodiment 38. The method of embodiment 36 or embodiment 37, wherein the host cell is autologous to the subject.

Embodiment 39. The method of any one of embodiments 36-38, wherein the subject expresses HLA-DPA1*01:03, HLA-DPB1*04:01 and/or HLA-DPB1*04:02.

Embodiment 40. A method of making transduced T cells expressing a T cell receptor (TCR) having antigenic specificity for a mutant form of the rearranged during transfection (RET) proto-oncogene with a methionine to threonine substitution at position 918 of SEQ ID NO: 11, the method comprising:

obtaining a population of lymphocytes from a subject;

contacting the population of lymphocytes with an anti-CD3 antibody and interleukin-2 to produce a population of activated T cells; and transducing the population of activated T cells with the vector of any one of embodiments 25-29, thereby producing the transduced T cells.

Embodiment 41. The method of embodiment 40, further comprising expanding the population of transduced T cells.

Embodiment 42. The method of embodiment 40 or embodiment 41, wherein the lymphocytes are obtained from a subject with medullary thyroid cancer.

The following examples are provided to illustrate certain particular features and/or embodiments. These examples should not be construed to limit the disclosure to the particular features or embodiments described.

EXAMPLES

Example 1

T Cell Receptors Specific for the RET M918T Mutation

Multiple HLA-DPA1*01:03/HLA-DPB1*04:01 (and potentially HLA-DPB1*04:02) restricted T-cell receptors (TCRs) have been identified that target the RET M918T hotspot mutation. This discovery allows for the development of TCR-gene therapy for patients whose cancers express HLA-DPA1*01:03/HLA-DPB1*04:01/02 and the RET M918T somatic mutation. The RET M918T mutation is most frequently found in sporadic medullary thyroid cancer (MTC), being present in approximately 30-40% of sporadic MTC cases (Romei et al., *Nat Rev Endocrinol* 12(4): 192-202, 2016). MTC is a rare cancer comprising ~3% of all thyroid cancers (American Cancer Society). The RET M918T mutation is also found in other cancer types such as adrenal cancer, cancer of the meninges, and others, but at much lower frequencies (COSMIC database).

The HLA-DPA1*01:03 allele is very common, and comprises about 60% of all HLA-DPA genes (Sidney et al., *J Immunol* 184: 2492-2503, 2010). HLA-DPB1*04:01 and HLA-DPB1*04:02 alleles are expressed by approximately 47-65%, and 17-22%, respectively, of Caucasians in the United States, which makes these alleles among the most common HLA class II alleles expressed by Caucasians (allelefrequencies.net). The HLA-DPB1*04:01/02 alleles are also expressed by other ethnicities at relatively high frequencies, such as African American (~16%/~17%), and Mexican American (~32%/~64%). Based on the frequency of MTC, the RET M918T mutation, and the HLA-DPB1*04:01/02 alleles, it is estimated that hundreds of patients in the United States with advanced MTC or other cancers that express the RET M918T mutation may be eligible for treatment with one or more of these TCRs.

TCR-ID-1, TCR-ID-2 and TCR-ID-3 were identified from a patient with sporadic MTC (CRI-2366) whose tumor harbored the RET M918T mutation as determined by whole exome sequencing. TCR-ID-1 was identified by in vitro stimulation of $10^6$ PBMC from patient CRI-2366 with 10 μg/mL RET long peptide (a 25 amino acid peptide containing the M918T mutation; SEQ ID NO: 10) and 10 IU/mL IL-2 and 10 ng/mL IL-7. This was performed in a G-Rex 24-well plate. After 14 days, cells were co-cultured with autologous immature dendritic cells (DC) pulsed with the RET M918T peptide. CD4+ T cells were identified that specifically upregulated the T-cell activation markers 4-1BB and OX40 upon RET M918T stimulation and these cells were sorted using a fluorescence activated cell sorter (FACS). RNA was isolated from the sorted cells and the TCRs were sequenced using the SMARTer human TCR a/b profiling kit (Takara). The dominant TCR-alpha and TCR-beta chains were designated as TCR-ID-1 (Table 1).

TCR-ID-2 was identified by stimulating CRI-2366 peripheral blood CD4 memory T cells, which were isolated using the EasySep human memory CD4+ T-cell isolation kit (StemCell Technologies), with autologous immature DC pulsed with 10 μg/mL RET long peptide (SEQ ID NO: 10). Details of cell culture conditions are described in Cafri et al. (*Nature Commun* 10: 449, 2019). Briefly, $0.5\times10^6$ memory CD4 cells were mixed with $0.125\times10^6$ per ml RET M918 peptide pulsed DCs in 500 μl of 50/50 medium with 30 ng/ml IL-21 in a well of a 48-well plate. After 72 hours, 500 μl of 50/50 medium containing 60 ng/ml of IL-21 and 6000 IU/ml of IL-2 were added to well and incubated for 72 hours. On day 7, cells were transferred into a new single well of a 12-well plate with 2 ml of 30 ng/ml IL-21 containing 3000 IU/ml IL-2. After 2 days, cells were transferred into a new single well of a 6-well plate containing 4 ml of 50/50 media with 30 ng/ml IL-21 containing 3000 IU/ml IL-2 and cultured for 72 hours. After the end of the first stimulation, cells were cocultured with autologous DC pulsed with RET M918T peptide and T cells that upregulated the T-cell activation markers 4-1BB and OX40 were sorted using FACS. RNA was isolated from the sorted cells followed by cDNA synthesis using the Smart-Seq2 protocol (Picelli et al., *Nat Protocols* 9: 171-181, 2014). TCRs were amplified with TCR-specific primers and libraries were constructed with the Nextera XT DNA Library prep kit followed by sequencing with an Illumina iSeq sequencer with 150 bp pair-end reads. The dominant TCR-alpha and TCR-beta chains were designated as TCR-ID-2 (Table 1).

TCR-ID-3 was identified by using an in vitro stimulation protocol derived from Pathangey et al. (*Oncotarget* 8:10785-10808, 2017). This protocol uses reagents to activate innate immunity (e.g., APC) in combination with antigen (RET M918T peptide) to drive expansion of antigen-reactive T cells from the blood. In brief, PBMC from patient CRI-2366 were cultured with GM-CSF (Leukine) and the TLR agonists R848 and LPS in combination with high-purity RET M918T long peptide (SEQ ID NO: 10). The peptide is taken up by APCs and presented to T cells within the culture. IL-7 was added to the cultures to promote expansion of the neoantigen-reactive T cells. After 14 days, the cultures were evaluated for reactivity against RET M918T. Reactive (CD4) T cells (as determined by 4-1BB upregulation upon RET M918T stimulation) were sorted by fluorescence activated cell sorting (FACS), followed by RNA isolation and cDNA synthesis using the Smart-Seq2 protocol (Picelli et al., *Nat Protocols* 9: 171-181, 2014). TCRs were amplified with TCR specific primers targeting the alpha and beta constant regions and libraries were constructed with the Nextera XT DNA Library prep kit followed by sequencing with an Illumina iSeq sequencer with 150 bp paired reads. The TCR alpha and beta chain sequences of the RET M918T-reactive TCR are shown in Table 1 below.

The genes encoding TCR-ID-1, TCR-ID-2 and TCR-ID-3 were synthesized and cloned into the MSGV1-retroviral vector (example schematic shown in FIG. 1). TCR-ID-1 was constructed with the TCR-alpha variable chain sequence (TRAV) followed by the murine TCR-alpha chain constant region (mTRAC), a P2A linker sequence, the TCR-beta variable sequence (TRBV), and the murine TCR-beta constant region (mTRBC). The use of murine (instead of human) TCR-alpha and beta constant chain sequences promotes pairing of the introduced TCR-alpha and beta chains and decreases the frequency of mispairing of the introduced TCRs with the endogenous TCRs (Cohen, et al., *Cancer Res* 66: 8878-8886, 2006). Moreover, enhanced expression and pairing of the introduced TCR-alpha and beta chains is also achieved by incorporating hydrophobic amino acids in the TCR alpha constant chain (Haga-Friedman et al., *J Immunol* 188: 5538-5546, 2012), and introducing a second disulfide bond between the alpha and beta chain constant regions (Cohen et al., *Cancer Res* 67: 3898-3903, 2007), respectively. Other technologies, such as lentiviruses, Crispr/Cas9, and transposon/transposase could be used to introduce the TCRs into T cells for therapeutic use.

Figures 2A, 2B:
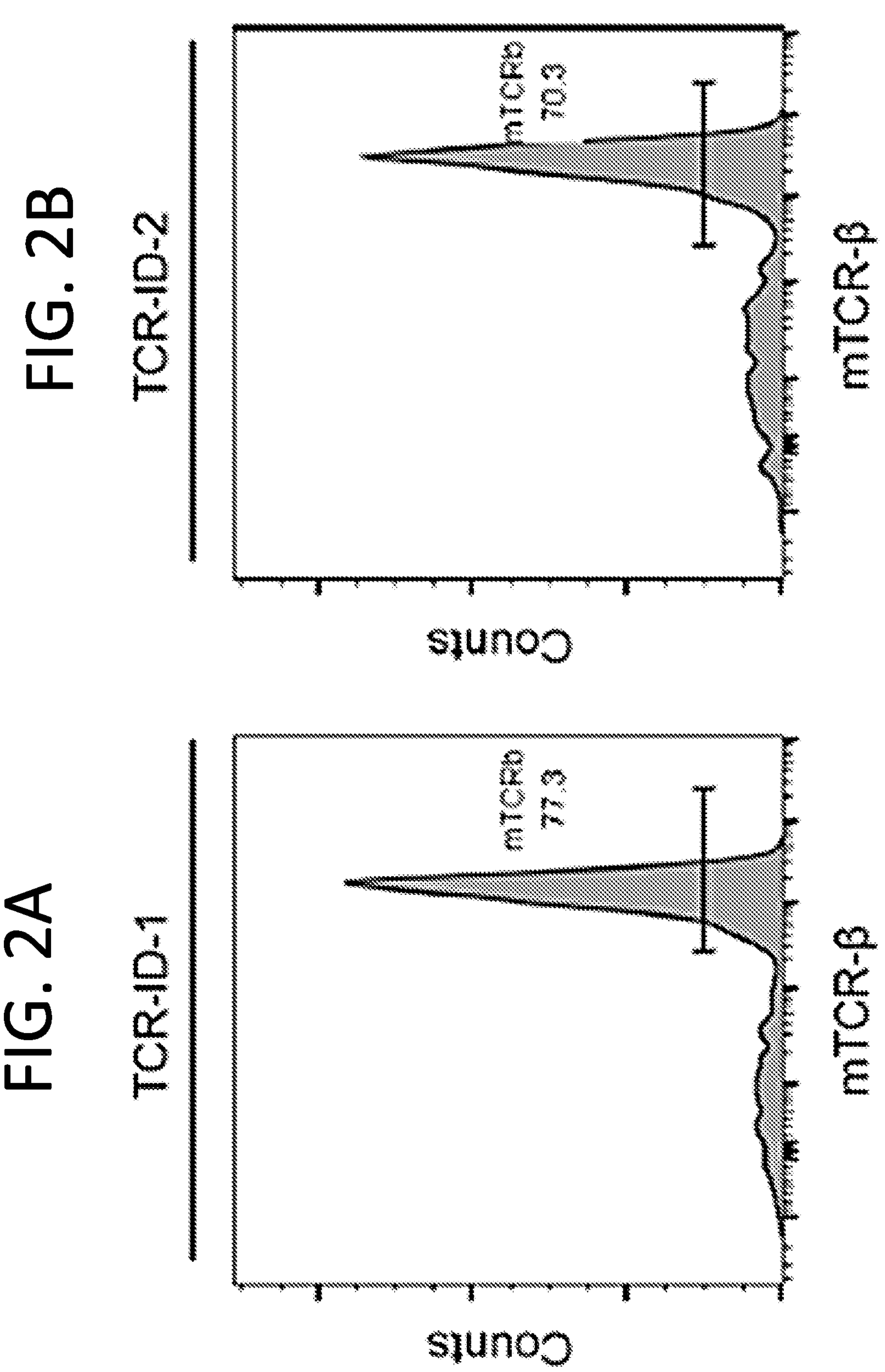
FIGS. 2A-2B: Expression of RET-M918T-reactive TCRs. Autologous peripheral blood T cells from patient CRI-2366 were stimulated with anti-CD3 antibody (OKT3) and IL-2 (300 IU/mL) for two days and then transduced with retrovirus encoding TCR-ID-1 (FIG. 2A) or TCR-ID-2 (FIG. 2B). Flow cytometry was used to detect expression of the mouse TCR-beta constant region, which is engineered into the introduced TCRs.

Retrovirus encoding TCR-ID-1 or TCR-ID-2 were made and used to genetically engineer peripheral blood T cells according to previously described methods (Tran et al., *N Engl J Med* 375: 2255-2262, 2016, which is herein incorporated by reference in its entirety). Approximately 70% of the T cells expressed TCR-ID-1 or TCR-ID-2 as determined by evaluating expression of the mouse TCR-beta constant region by flow cytometry (FIGS. 2A-2B).

Figures 3A, 3B:
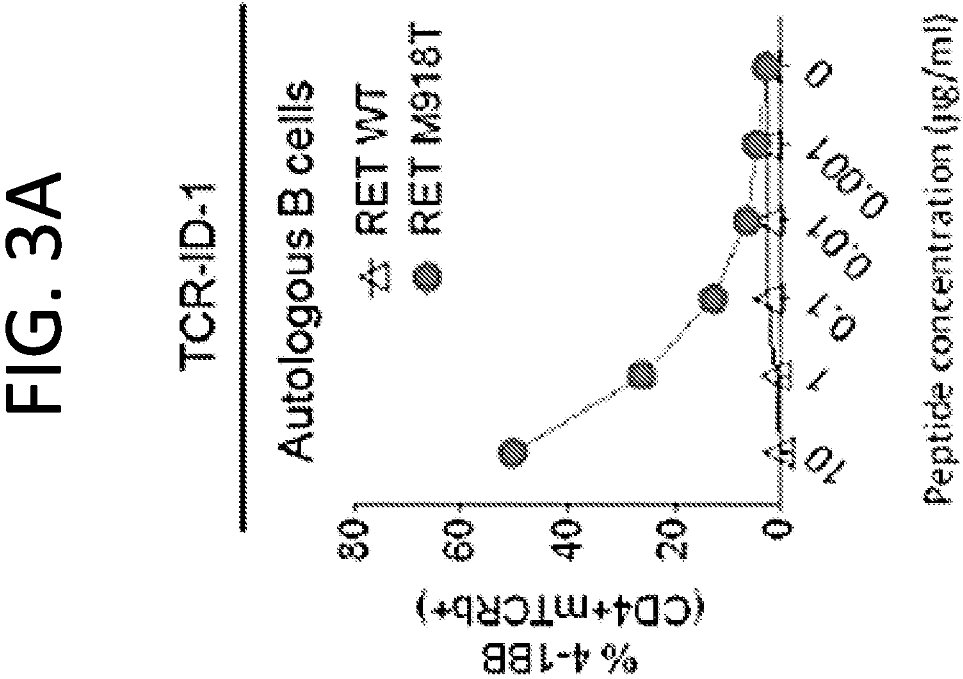
FIGS. 3A-3F: Validation of RET-M918T-reactive TCRs.
Figures 3C, 3D:
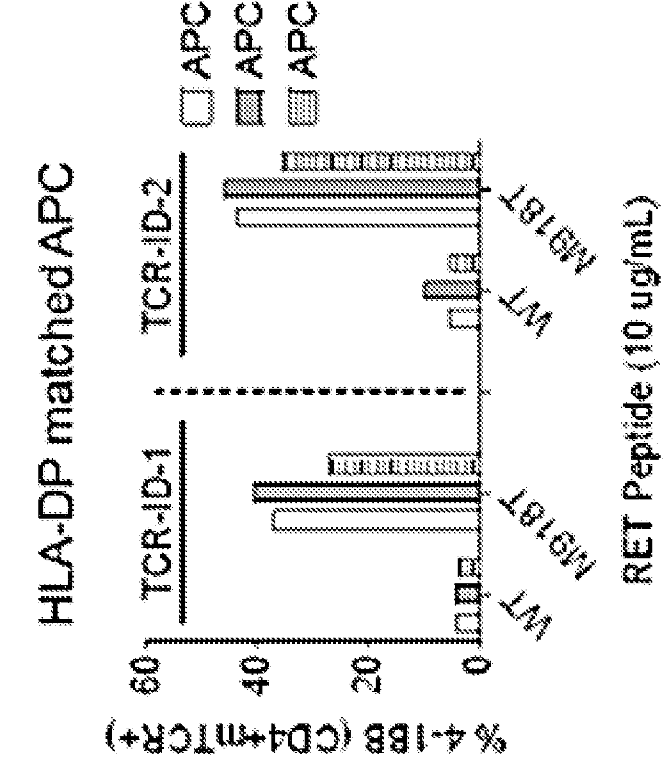
Figure 3F:
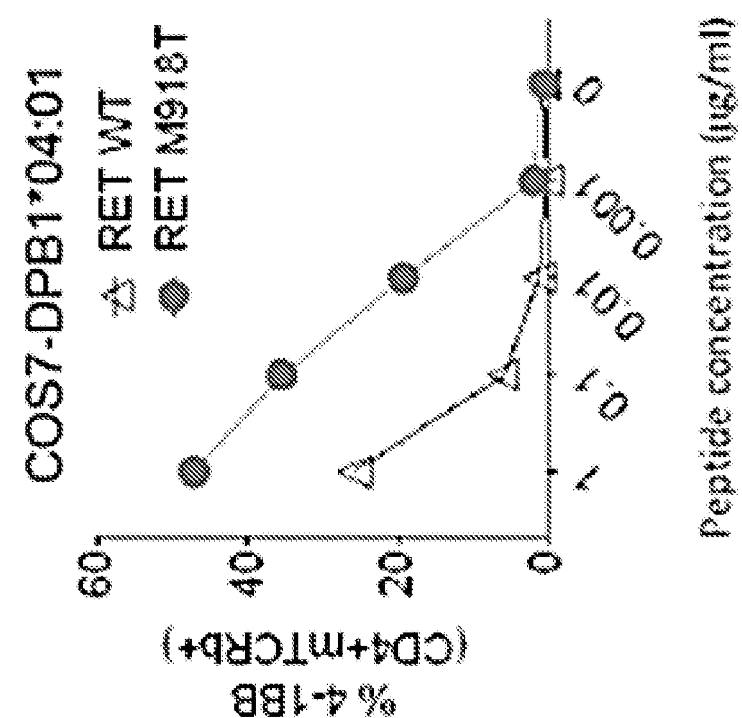
Figure 3E:
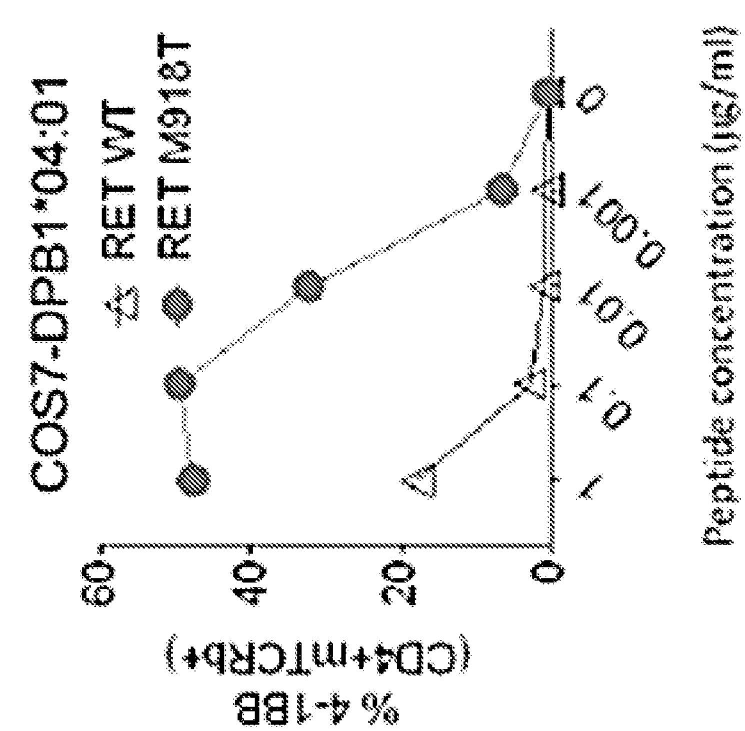

These TCR transduced T cells were then tested for reactivity against wild type (WT) and mutant RET M918T peptides (Table 3). As shown in FIGS. 3A-3F, autologous peripheral blood T cells expressing either TCR-ID-1 (FIG. 3A) or TCR-ID-2 (FIG. 3B) specifically recognized mutant RET M918T-peptide pulsed autologous B cells. In addition, it appeared that the TCRs recognized RET M918T when presented by HLA-DP class-II molecules. Patient CRI-2366 is homozygous at the HLA-DP locus, and expresses the HLA-DPA1*01:03 and HLA-DPB1*04:01 combination (hereafter referred to as "DPB1*04:01"). Thus, it was tested whether the TCR transduced T cells recognized RET M918T in the context of DPB1*04:01. To that end, allogeneic PBMC were identified that were either matched or mismatched with CRI-2366 at the HLA-DP locus. As shown in FIG. 3C, T cells transduced to express TCR-ID-1 or TCR-ID-2 recognized RET M918T peptide when presented by allogeneic PBMC from 3 different patients who expressed DPB1*04:01. In contrast, the TCR-transduced T cells did not recognize RET M918T peptide pulsed allogeneic PBMC from 2 other patients who did not express DPB1*04:01 (FIG. 3D, mock), but reactivity to RET M918T was restored when DPB1*04:01 was introduced into these HLA-DP mismatched PMBC (FIG. 3D, DPB1*04:01). To further demonstrate the requirement of the specific HLA-DP alleles for recognition of the RET M918T peptide by the TCR engineered T cells, the COS-7 monkey cell line was transfected with DPB1*04:01, pulsed with titrating amounts of the WT RET (SEQ ID NO: 9) or RET M918T (SEQ ID NO: 10) peptides, and then cocultured with the TCR-engineered T cells. FIGS. 3E and 3F show recognition of RET M918T by TCR-ID-1 and TCR-ID-2, respectively, when the COS-7 cells were transfected with DPB1*0401.

Figures 4A, 4B:
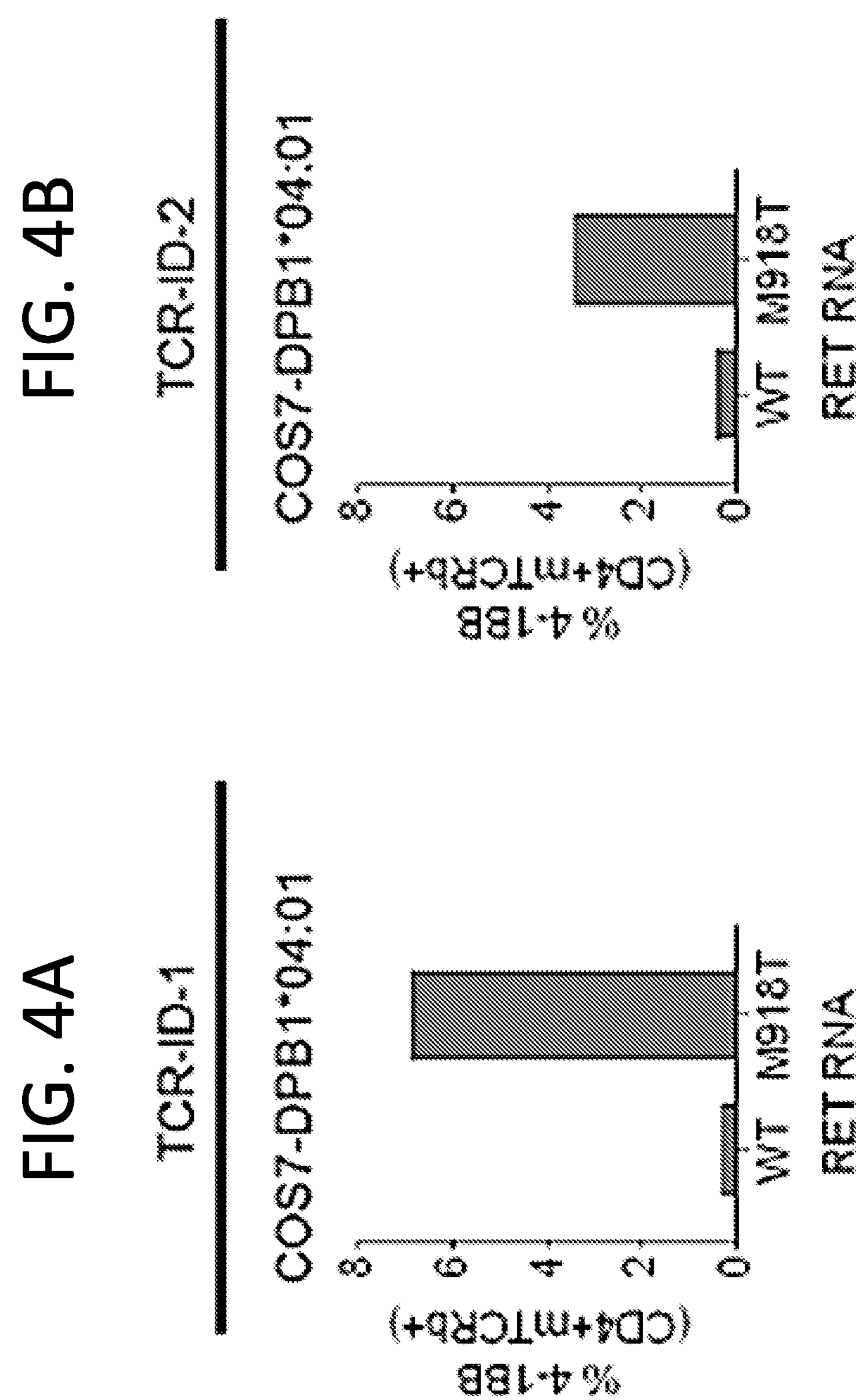
FIGS. 4A-4D: Recognition of cells expressing the RET-M918T gene by RET M918T-reactive TCR-transduced T cells.
Figures 4C, 4D:
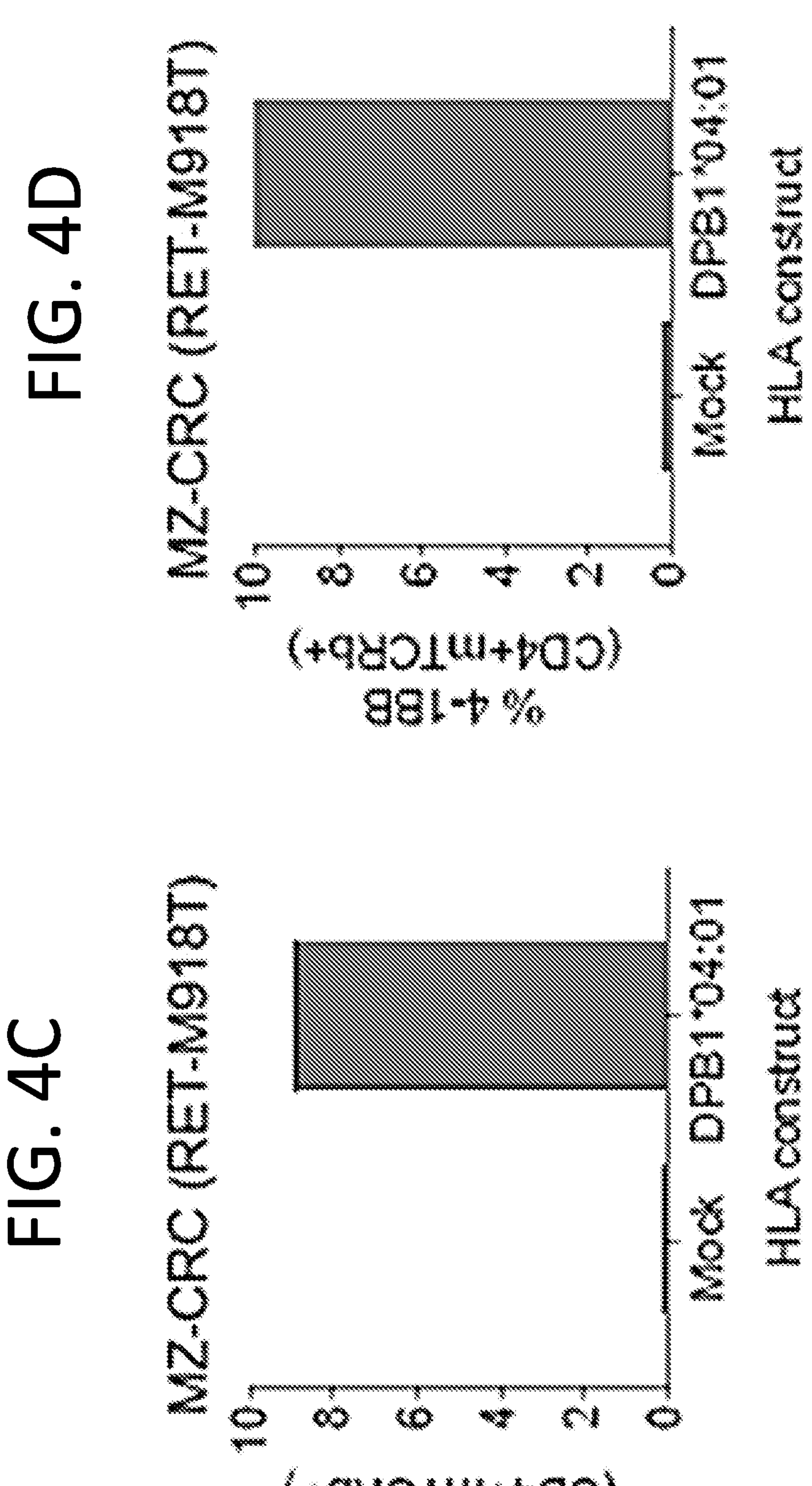
Figures 5A, 5B:
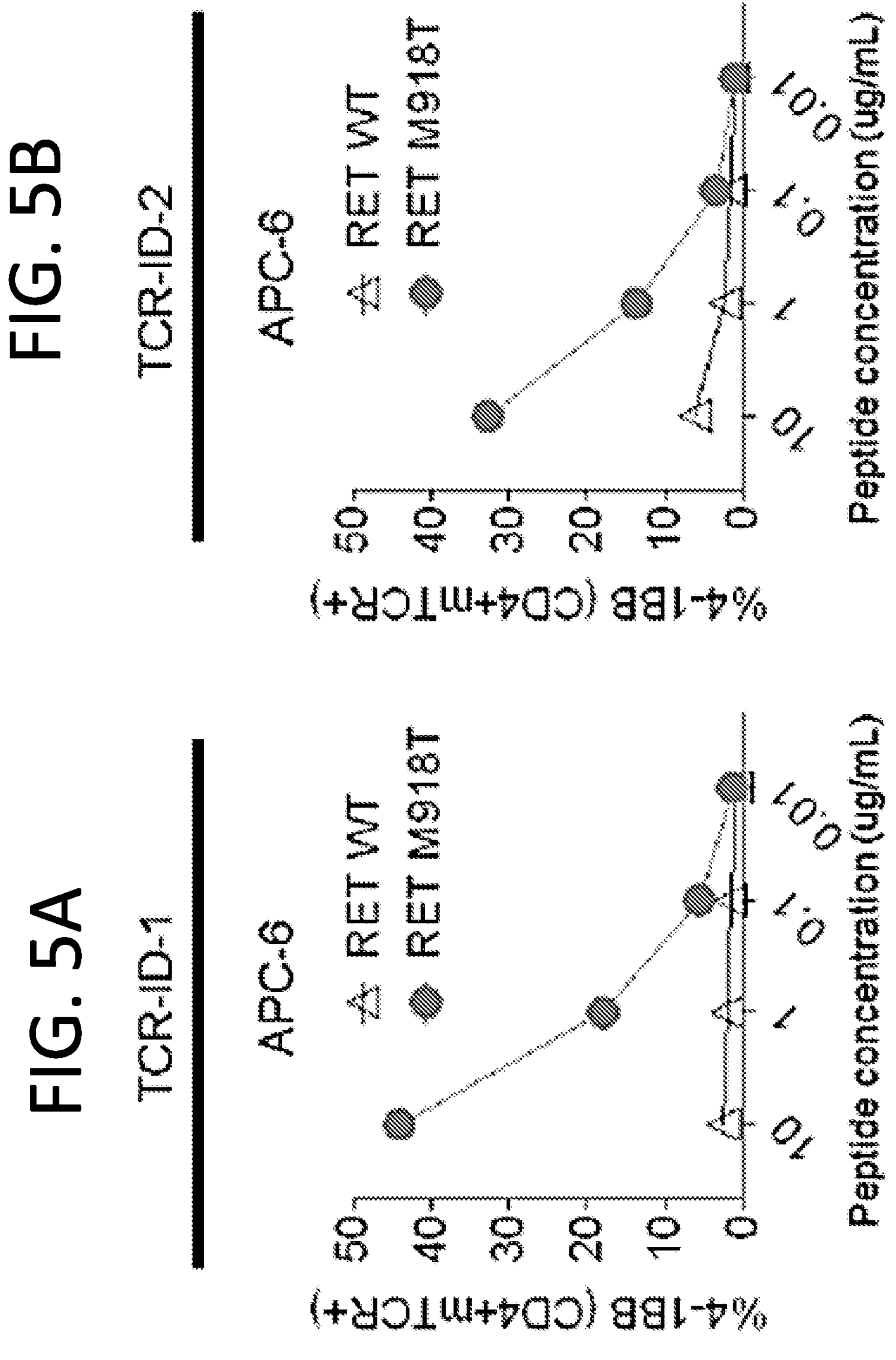
FIGS. 5A-5F: RET M918T-reactive TCR-transduced T cells can recognize RET-M918T in the context of HLA-DPB1*04:02. T cells transduced to express TCR-ID-1 (FIGS. 5A, 5C, 5E) or TCR-ID-2 (FIGS. 5B, 5D, 5F) were cocultured overnight with allogeneic PBMC from three different donors (APC-6, -7, -8), which express the HLA-DPB1*04:02 molecule, that were pulsed with titrating amounts of wild-type (WT) or M918T RET peptide, and flow cytometry was used to evaluate 4-1BB on the transduced T cells.
Figure 5D:
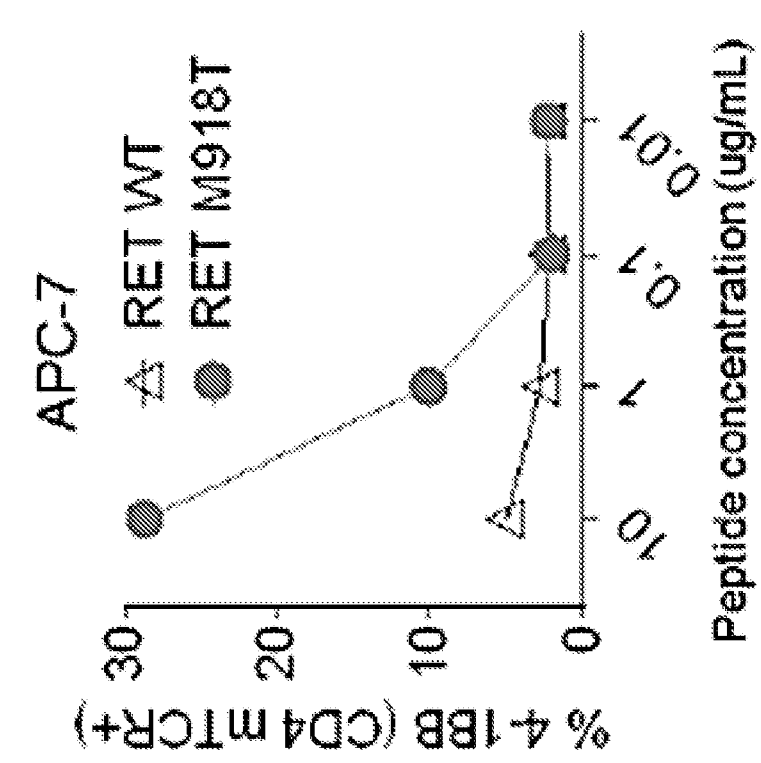
Figure 5C:
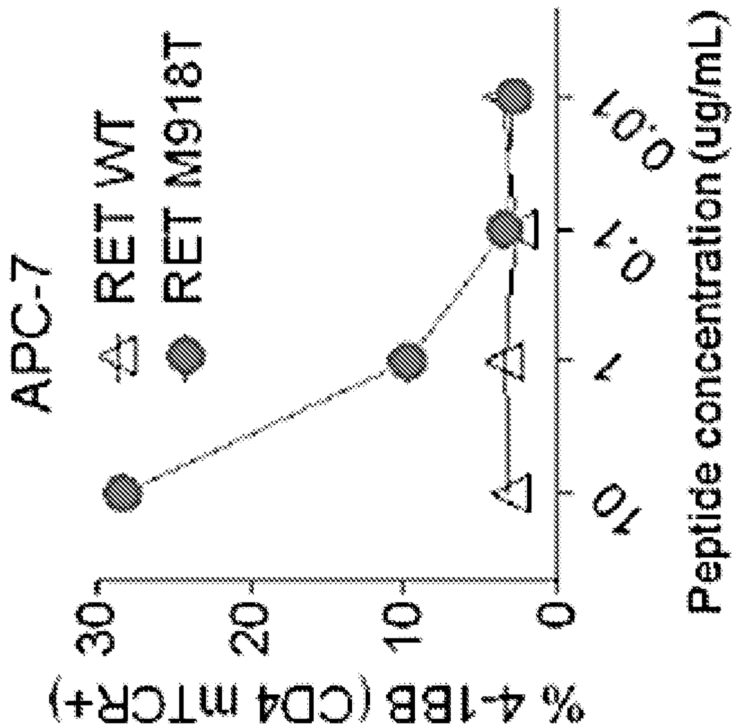
Figures 5E, 5F:
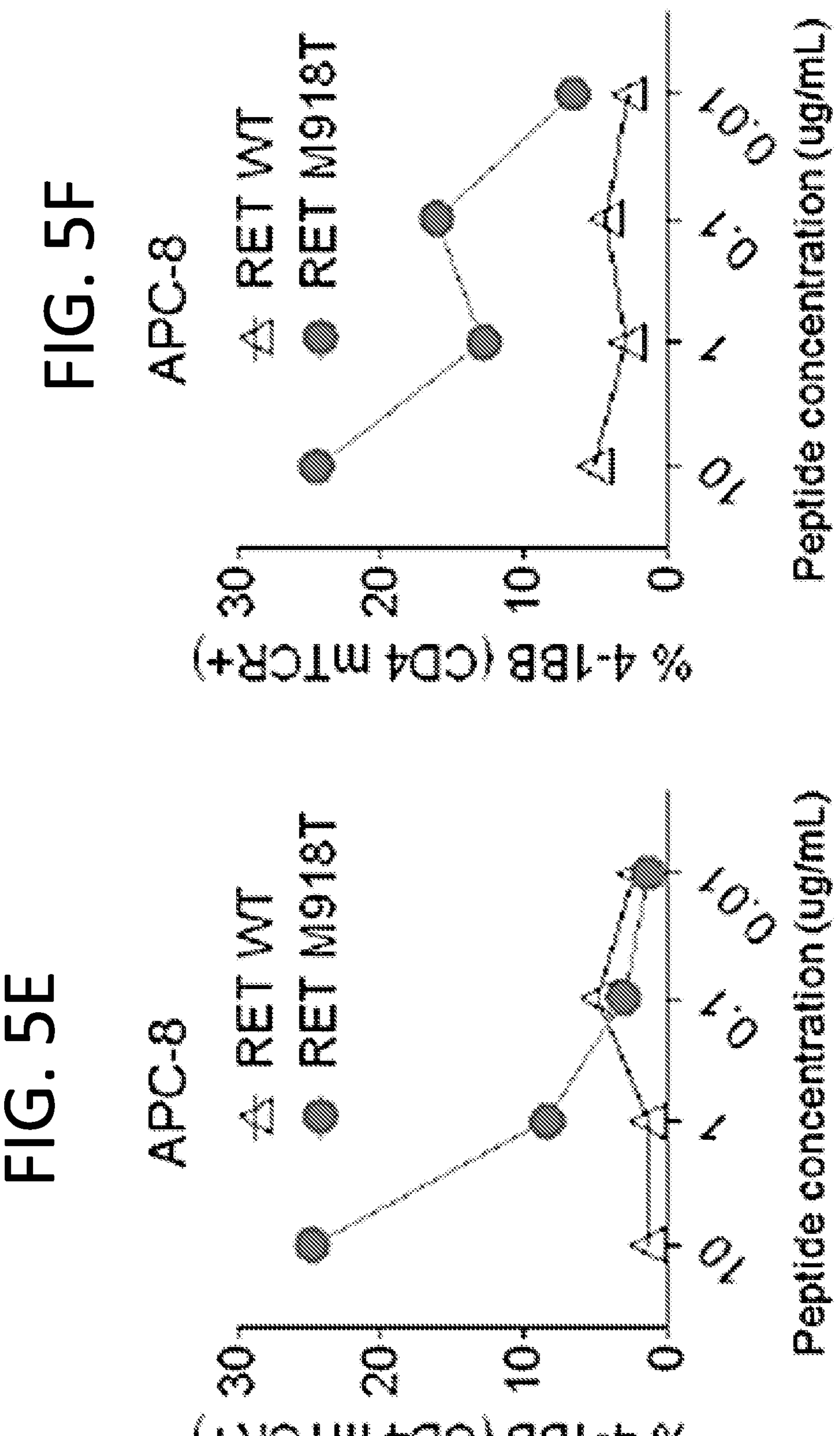

CD4+ T cells often recognize antigens that are taken up by antigen presenting cells through the exogenous pathway whereby antigen is endocytosed into the cell, degraded in acidic lysosomes, and the peptides ultimately loaded onto MHC (HLA) class II molecules. The experiments described thus far demonstrate that TCR-ID-1 and TCR-ID-2 can recognize mutated RET M918T peptide when delivered through the exogenous pathway. To determine whether the transduced T cells can recognize endogenously expressed RET M918T mutation (i.e., when the mutation is genetically expressed within a cell), T cells transduced with either TCR-ID-1 or TCR-ID-2 were cocultured with COS-7 cells that were cotransfected with DPB1*04:01 and either the WT RET gene or RET M918T mutated gene. As shown in FIGS. 4A and 4B, both TCRs recognized COS-7 cells when cotransfected with DPB1*04:01 and RET M918T gene but not WT RET gene, although the reactivity was weaker than RET M918T peptide-pulsed COS-7 cells (FIGS. 3E and 3F). Similarly, the TCR-engineered T cells recognized the medullary cancer cell line MZ-CRC, which naturally harbors and expresses the RET M918T mutation, only when DPB1*04:01 was transfected into the cell line (FIGS. 4C and 4D).

The HLA-DPB1*04:01 allele is one of the most common HLA alleles expressed by the human population. The closely related allele HLA-DPB1*04:02 differs from DPB1*04:01 by only 4 amino acids and is expressed by a moderately high frequency of humans. Given this, it was tested whether TCR-ID-1 and TCR-ID-2 could recognize RET M918T in the context of DPB1*04:02 in addition to DPB1*04:01. T cells transduced with either TCR-ID-1 or TCR-ID-2 were cocultured with allogeneic PBMC from 3 different patients who express the DPB1*04:02 allele that were pulsed with titrating amounts of RET WT (SEQ ID NO: 9) or RET M918T (SEQ ID NO: 10) peptide. FIGS. 5A-5F demonstrate that TCR-ID-1 and TCR-ID-2 specifically recognized RET M918T peptide when pulsed on all 3 DPB1*04:02-positive patient PBMC. The ability of TCR-ID-1 and TCR-ID-2 to recognize RET M918T in both DPB1*04:01 and DPB1*04:02 extends the number of potential patients that could be treated with these TCRs.

Figures 6A, 6B, 6C:
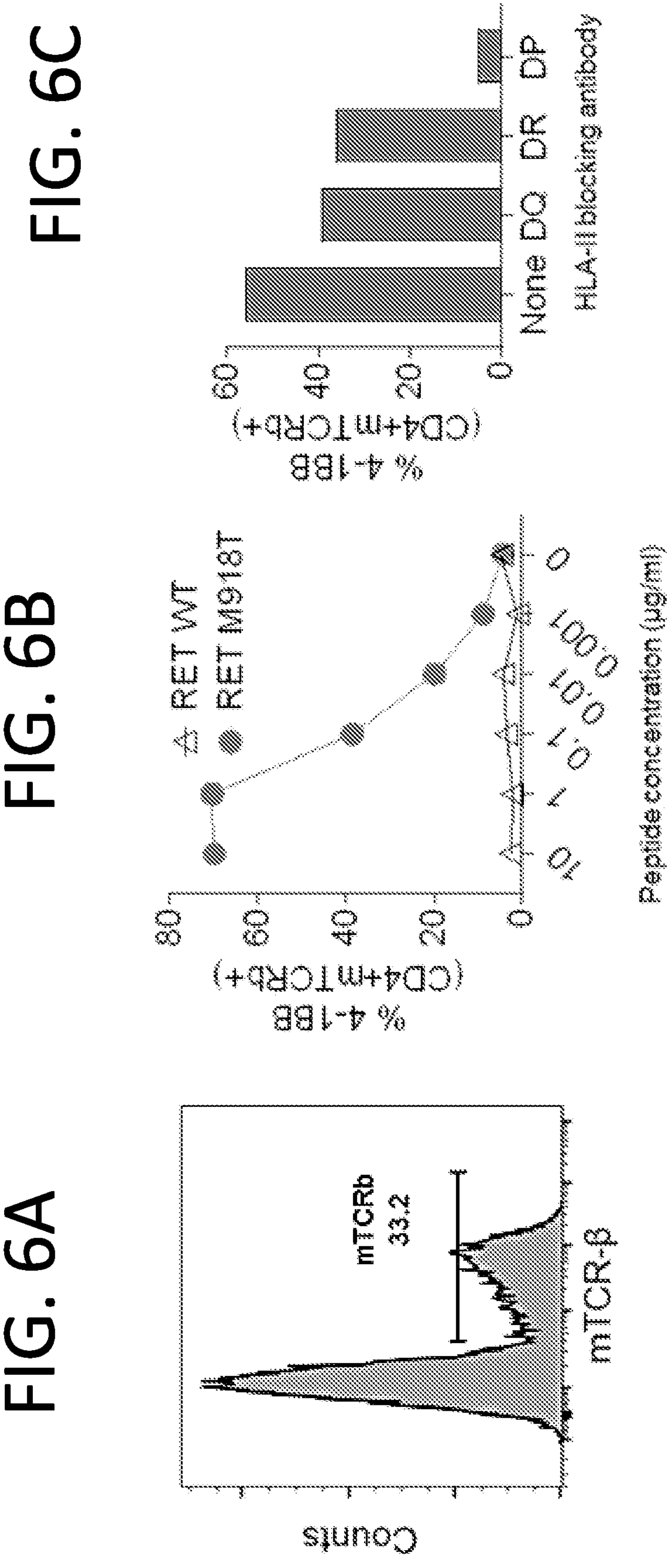
FIGS. 6A-6G: Characterization of RET M918T-reactive TCR-ID-3.
Figures 6D, 6E, 6F, 6G:
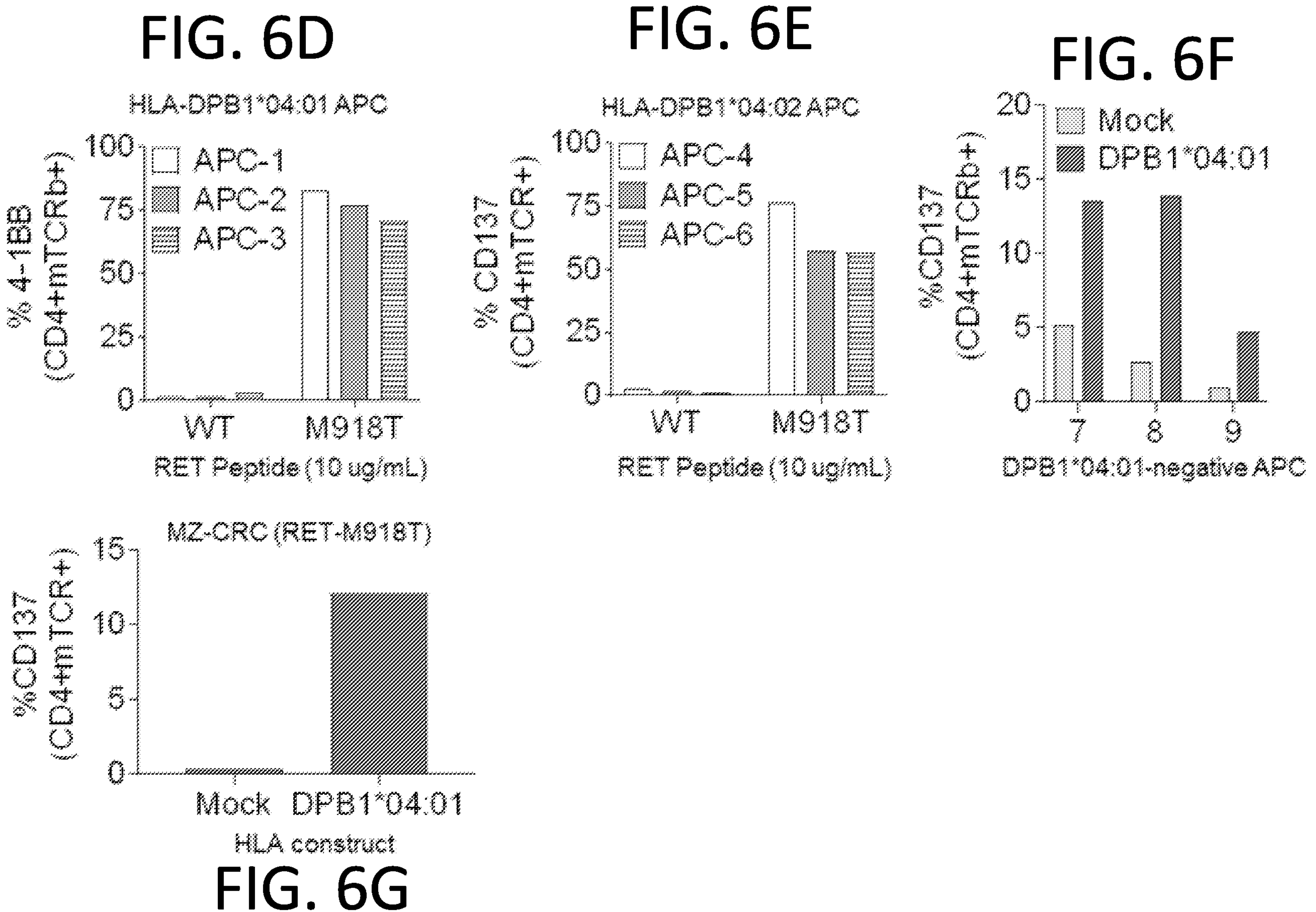

The genes encoding TCR-ID-3 were cloned into the MSGV1 retroviral vector as described for TCR-ID-1 and TCR-ID-2. Retrovirus encoding TCR-ID-3 was then made and used to genetically engineer peripheral blood T cells. Approximately 33% of the T cells expressed TCR-ID-3 as determined by evaluating expression of the mouse TCR-beta constant region by flow cytometry (FIG. 6A). The TCR-transduced T cells were then tested for reactivity against wild type (WT) and mutant RET M918T peptides (Table 3). As shown in FIG. 6B, autologous peripheral blood T cells expressing TCR-ID-3 specifically recognized mutant RET M918T-peptide pulsed autologous B cells. FIG. 6C shows that the TCR recognized RET M918T when presented by HLA-DP class-II molecules. Patient CRI-2366 is homozygous at the HLA-DP locus, and expresses the HLA-DPA1*01:03 and HLA-DPB1*04:01 combination (hereafter referred to as "DPB1*04:01"). Thus, it was tested whether the TCR transduced T cells recognized RET M918T in the context of DPB1*04:01. To that end, allogeneic PBMC that were either matched or mismatched with CRI-2366 at the HLA-DP locus were identified. As shown in FIG. 6D, T cells transduced to express TCR-ID-3 recognized RET M918T peptide when presented by allogeneic PBMC from 3 different patients who expressed DPB1*04:01. The TCR-ID-3 transduced T cells also recognized RET M918T when presented on allogeneic PBMC from 3 different patients who expressed the highly similar DPB1*04:02 allele (FIG. 6E). In contrast, minimal recognition of RET M918T was observed when the TCR-transduced T cells were cocultured with allogeneic PBMC from 3 other patients who did not express DPB1*04:01 or DPB1*04:02 (FIG. 6F, Mock), unless the DPB1*04:01 was transfected into the PBMC (FIG. 6F, DPB1*04:01). Similarly, the TCR-ID-3 transduced T cells recognized endogenously expressed RET M918T mutation (when the mutation is genetically expressed within a cell), only when the cell line was transfected with the HLA-DPA1*01:03/DPB1*04:01 alleles, as demonstrated by reactivity against the medullary cancer cell line MZ-CRC, which naturally harbors and expresses the RET M918T mutation (FIG. 6G).

TABLE 1

TCR-alpha and TCR-beta nucleotide and amino acid sequences that are reactive to the RET-M918T neoantigen (leader sequences are italicized and CDR sequences are in bold)

| TCR-ID | TCR chain | Nucleotide | SEQ ID NO: | Amino acid | SEQ ID NO: |
|---|---|---|---|---|---|
| 1 | Alpha (TRAV9-2*01) | *ATGAACTATTCTCC*<br>*AGGCTTAGTATCTC*<br>*TGATACTCTTACTG*<br>*CTTGGAAGAACCCG*<br>*T*GGAAATTCAGTGA<br>CCCAGATGGAAGGG<br>CCAGTGACTCTCTC<br>AGAAGAGGCCTTCC<br>TGACTATAAACTGC<br>ACGTACACA**GCCA**<br>**CAGGATACCCTTC**<br>**C**CTTTTCTGGTAT<br>GTCCAATATCCTG<br>GAGAAGGTCTACA<br>GCTCCTCCTGAAA<br>**GCCACGAAGGCTG**<br>**ATGACAAG**GGAAG<br>CAACAAAGGTTTT<br>GAAGCCACATACC<br>GTAAAGAAACCAC<br>TTCTTTCCACTTG<br>GAGAAAGGCTCAG<br>TTCAAGTGTCAGA<br>CTCAGCGGTGTAC<br>TTCTGT**GCTCTGA**<br>**GTGAGAACGCCGG**<br>**TAACCAGTTCTAT**<br>TTTGGGACAGGGA<br>CAAGTTTGACGGT<br>CATTCCAA | 1 | *MNYSPG*<br>*LVSLIL*<br>*LLLGRT*<br>*R*GNSVT<br>QMEGPV<br>TLSEEA<br>FLTINC<br>TYT**ATG**<br>**YPS**LFW<br>YVQYPG<br>EGLQLL<br>LK**ATKA**<br>**DDK**GSN<br>KGFEAT<br>YRKETT<br>SFHLEK<br>GSVQVS<br>DSAVYF<br>C**ALSEN**<br>**AGNQFY**<br>FGTGTS<br>LTVIP | 2 |
| 1 | Beta (TRBV6-5*01) | *ATGAGCATCGGCC*<br>*TCCTGTGCTGTGC*<br>*AGCCTTGTCTCTC*<br>*CTGTGGGCAGGTC*<br>*CAGTG*AATGCTGG<br>TGTCACTCAGACC<br>CCAAAATTCCAGG<br>TCCTGAAGACAGG<br>ACAGAGCATGACA<br>CTGCAGTGTGCCC<br>AGGAT**ATGAACCA**<br>**TGAATAC**ATGTCC<br>TGGTATCGACAAG<br>ACCCAGGCATGGG<br>GCTGAGGCTGATT<br>CATTAC**TCAGTTG**<br>**GTGCTGGTATC**AC<br>TGACCAAGGAGAA<br>GTCCCCAATGGCT<br>ACAATGTCTCCAG<br>ATCAACCACAGAG<br>GATTTCCCGCTCA<br>GGCTGCTGTCGGC<br>TGCTCCCTCCCAG<br>ACATCTGTGTACT<br>TCTGT**GCCAGCAG**<br>**CCGAGGGAATACG**<br>**CAGTAT**TTTGGCC<br>CAGGCACCCGGCT<br>GACAGTGCTCG | 3 | *MSIGLL*<br>*CCAALS*<br>*LLWAGP*<br>*V*NAGVT<br>QTPKFQ<br>VLKTGQ<br>SMTLQC<br>AQD**MNH**<br>**EY**MSWY<br>RQDPGM<br>GLRLIH<br>**YSVGAG**<br>ITDQGE<br>VPNGYN<br>VSRSTT<br>EDFPLR<br>LLSAAP<br>SQTSVY<br>FC**ASSR**<br>**GNTQYF**<br>GPGTRL<br>TVL | 4 |
| 2 | Alpha (TRAV14/DV4*02) | *ATGTCACTTTCTA*<br>*GCCTGCTGAAGGT*<br>*GGTCACAGCTTCA*<br>*CTGTGGCTAGGAC*<br>*CTGGCATT*GCCCA<br>GAAGATAACTCAA<br>ACCCAACCAGGAA<br>TGTTCGTGCAGGA | 5 | *MSLSSL*<br>*LKVVTA*<br>*SLWLGP*<br>GIAQKI<br>TQTPQG<br>MFVQEK<br>EAVTLD<br>CTYD**TS** | 6 |

TABLE 1-continued

TCR-alpha and TCR-beta nucleotide and amino acid sequences that are reactive to the RET-M918T neoantigen (leader sequences are italicized and CDR sequences are in bold)

| TCR-ID | TCR chain | Nucleotide | SEQ ID NO: | Amino acid | SEQ ID NO: |
|---|---|---|---|---|---|
| | | AAAGGAGGCTGTG<br>ACTCTGGACTGCA<br>CATATGAC**ACCAG**<br>**TGATCAAAGTTAT**<br>**GGT**CTATTCTGGT<br>ACAAGCAGCCCAG<br>CAGTGGGGAAATG<br>ATTTTTCTTATTT<br>AT**CAGGGGTCTTA**<br>**TGACGAGCAAAAT**<br>GCAACAGAAGGTC<br>GCTACTCATTGAA<br>TTTCCAGAAGGCA<br>AGAAAATCCGCCA<br>ACCTTGTCATCTC<br>CGCTTCACAACTG<br>GGGGACTCAGCAA<br>TGTATTTCTGT**GC**<br>**AATGAGAGAGGGC**<br>**GATGGTGATGACA**<br>**TGCGC**TTTGGAGC<br>AGGGACCAGACTG<br>ACAGTAAAACCAA | | **DQSYG**L<br>FWYKQP<br>SSGEMI<br>FLIY**QG**<br>**SYDEQN**<br>ATEGRY<br>SLNFQK<br>ARKSAN<br>LVISAS<br>QLGDSA<br>MYFC**AM**<br>**REGDGD**<br>**DMR**FGA<br>GTRLTV<br>KP | |
| 2 | Beta (TRBV2*01) | *ATGGATACCTGGC*<br>*TCGTATGCTGGGC*<br>*AATTTTTAGTCTC*<br>*TTGAAAGCAGGAC*<br>*TCACA*GAACCTGA<br>AGTCACCCAGACT<br>CCCAGCCATCAGG<br>TCACACAGATGGG<br>ACAGGAAGTGATC<br>TTGCGCTGTGTCC<br>CCATC**TCTAATCA**<br>**CTTATAC**TTCTAT<br>TGGTACAGACAAA<br>TCTTGGGGCAGAA<br>AGTCGAGTTTCTG<br>GTTTCC**TTTTATA**<br>**ATAATGAAATC**TC<br>AGAGAAGTCTGAA<br>ATATTCGATGATC<br>AATTCTCAGTTGA<br>AAGGCCTGATGGA<br>TCAAATTTCACTC<br>TGAAGATCCGGTC<br>CACAAAGCTGGAG<br>GACTCAGCCATGT<br>ACTTCTGT**GCCAG**<br>**CAGTTCTCAGATT**<br>**CAGACGGTCATGA**<br>**ACACTGAAGCTTT**<br>**C**TTTGGACAAGGC<br>ACCAGACTCACAG<br>TTGTAG | 7 | *MDTWLV*<br>*CWAIFS*<br>*LLKAGL*<br>*TE*PEVT<br>QTPSHQ<br>VTQMGQ<br>EVLRCV<br>PIS**NHL**<br>**Y**FYWYR<br>QILGQK<br>VEFLVS<br>**FYNNEI**<br>SEKSEI<br>FDDQFS<br>VERPDG<br>SNFTLK<br>IRSTKL<br>EDSAMY<br>FC**ASSS**<br>**QIQTVM**<br>**NTEAFF**<br>GQGTRL<br>TVV | 8 |
| 3 | Alpha (TRAV29DV5*01) | *ATGGCCATGCTCCT*<br>*GGGGGCATCAGTGC*<br>*TGATTCTGTGGCTT*<br>*CAGCCAGACTGGGT*<br>*AAACAGTCAACAGA*<br>*GAGAATAT*GACCAG<br>CAAGTTAAGCAAAA<br>TTCACCATCCCTGA<br>GCGTCCAGGAAGGA | 18 | *MAMLLG*<br>*ASVLIL*<br>*WLQPDW*<br>*VNSQQK*<br>*ND*DQQV<br>KQNSPS<br>LSVQEG<br>RISILN<br>CDYT**NS** | 19 |

TABLE 1-continued

TCR-alpha and TCR-beta nucleotide and amino acid sequences that are reactive to the RET-M918T neoantigen (leader sequences are italicized and CDR sequences are in bold)

| TCR-ID | TCR chain | Nucleotide | SEQ ID NO: | Amino acid | SEQ ID NO: |
|---|---|---|---|---|---|
| | | AGAATTTCTATTCTGAACTGTGACTATACT**AACAGCATGTTTGATTAT**TTCCTATGGTACAAAAAATACCCTGCTGAAGGTCCTACATTCCTGATATC**TATAAGTTCCATTAAGGATAAA**AATGAAGATGGAAGATTCACTGTCTTCTTAAACAAAAGTGCCAAGCACCTCTCTCTGCACATTGTGCCCTCCCAGCCTGGAGACTCTGCAGTGTACTTCTGT**GCAGCAAGCGGCCATGGAGGAAGCCAAGGAAATCTCATC**TTTGGAAAAGGCACTAAACTCTCTGTTAAACCAA | | **MFDYFL**WYKKYPAEGPTFLIS**ISSIKDK**NEDGRFTVFLNKSAKHLSLHIVPSQPGDSAVYFC**AASGHGGSQGNLIF**GKGTKLSVKP | |
| 3 | Beta (TRBV7-8*01) | *ATGGGCACCAGGCTCCTCTGCTGGGTGGTCCTGGGTTTCCTAGGGACAGATCACAC*AGGTGCTGGAGTCTCCCAGTCCCCTAGGTACAAAGTCGCAAAGAGAGGACAGGATGTAGCTCTCAGGTGTGATCCAAT**TTCGGGTCATGTATCC**CTTTTTTGGTACCAACAGGCCCTGGGGCAGGGGCCAGAGTTTCTGACTTAT**TTCCAGAATGAAGCTCAA**CTAGACAAATCGGGGCTGCCCAGTGATCGCTTCTTTGCAGAAAGGCCTGAGGGATCCGTCTCCACTCTGAAGATCCAGCGCACACAGCAGGAGGACTCCGCCGTGTATCTCTGT**GCCAGCAGCTTAAGGTTTTTGGGACAGGGCTCCTACGAGCAGTAC**TTCGGGCCGGGCACCAGGCTCACGGTCACAG | 20 | *MGTRLLCWVVLGFLGTDHTGAGVS*QSPRYKVAKRGQDVALRCDPI**SGHVS**LFWYQQALGQGPEFLTY**FQNEAQ**LDKSGLPSDRFFAERPEGSVSTLKIQRTQQEDSAVYLC**ASSLRFLGQGSYEQY**FGPGTRLTVT | 21 |

TABLE 2

Nucleotide and amino acid positions of the leader, CDR1, CDR2 and CDR3

| Alpha (TRAV9-2*01) | Nucleotides of SEQ ID NO: 1 | Amino acids of SEQ ID NO: 2 |
|---|---|---|
| Leader | 1-57 | 1-19 |
| CDR1 | 136-153 | 46-51 |
| CDR2 | 205-225 | 69-75 |
| CDR3 | 328-360 | 110-120 |

TABLE 2-continued

Nucleotide and amino acid positions of the leader, CDR1, CDR2 and CDR3

| Beta (TRBV2*01) | Nucleotides of SEQ ID NO: 3 | Amino acids of SEQ ID NO: 4 |
|---|---|---|
| Leader | 1-57 | 1-19 |
| CDR1 | 136-150 | 46-50 |
| CDR2 | 202-219 | 68-72 |
| CDR3 | 331-357 | 111-119 |
| **Alpha (TRAV14/DV4*02)** | **Nucleotides of SEQ ID NO: 5** | **Amino acids of SEQ ID NO: 6** |
| Leader | 1-60 | 1-20 |
| CDR1 | 139-159 | 47-53 |
| CDR2 | 211-234 | 71-78 |
| CDR3 | 337-369 | 113-123 |
| **Beta (TRBV2*01)** | **Nucleotides of SEQ ID NO: 7** | **Amino acids of SEQ ID NO: 8** |
| Leader | 1-57 | 1-19 |
| CDR1 | 136-150 | 46-49 |
| CDR2 | 202-219 | 67-72 |
| CDR3 | 334-378 | 111-125 |
| **Alpha (TRAV29DV5*01)** | **Nucleotides of SEQ ID NO: 18** | **Amino acids of SEQ ID NO: 19** |
| Leader | 1-78 | 1-26 |
| CDR1 | 157-174 | 53-58 |
| CDR2 | 226-246 | 76-82 |
| CDR3 | 349-387 | 117-129 |
| **Beta (TRBV7-8*01)** | **Nucleotides of SEQ ID NO: 20** | **Amino acids of SEQ ID NO: 21** |
| Leader | 1-57 | 1-19 |
| CDR1 | 136-150 | 46-50 |
| CDR2 | 202-219 | 68-73 |
| CDR3 | 334-378 | 112-126 |

TABLE 3

Amino acid sequences of wild type and mutated M918T RET peptides

| Peptide (25 amino acid) | Amino Acid Sequence | SEQ ID NO: |
|---|---|---|
| RET wild type | VKRSQGRIPVKW**M**AIESLFDHIYTT | 9 |
| RET M918T | VKRSQGRIPVKW**T**AIESLFDHIYTT | 10 |

Mouse alpha chain constant region (SEQ ID NO: 12)

XIQNPEPAVYQLKDPRSQDSTLCLFTDFDSQINVPKTMESGTFITDKCVL

DMKAMDSKSNGAIAWSNQTSFTCQDIFKETNATYPSSDVPCDATLTEKSF

ETDMNLNFQNLLVIVLRILLLKVAGFNLLMTLRLWSS, wherein X is N or D

The alpha chain constant region contains four amino acid substitutions relative to the wild-type mouse sequence, underlined in the sequence above. At residue 48, T is substituted with C to enable disulfide bonding with the beta chain. The remaining three substitutions introduce aliphatic amino acids: S112L, M114I and G115V.

```
Mouse constant beta chain 1
                                    (TCB1; SEQ ID NO: 13)
EDLRNVTPPKVSLFEPSKAEIANKQKATLVCLARGFFPDHVELSWWVNGK

EVHSGVCTDPQAYKESNYSYCLSSRLRVSATFWHNPRNHFRCQVQFHGLS

EEDKWPEGSPKPVTQNISAEAWGRADCGITSASYQQGVLSATILYEILLG

KATLYAVLVSTLVVMAMVKRKNS
```

The beta chain constant region contains a serine to cysteine amino acid substitution at residue 57 to enable disulfide bonding with the alpha chain.

```
Alternative constant region sequences:
Mouse constant beta chain 2
                                    (TCB2; SEQ ID NO: 14)
EDLRNVTPPKVSLFEPSKAEIANKQKATLVCLARGFFPDHVELSWWVNGK

EVHSGVSTDPQAYKESNYSYCLSSRLRVSATFWHNPRNHFRCQVQFHGLS

EEDKWPEGSPKPVTQNISAEAWGRADCGITSASYHQGVLSATILYEILLG

KATLYAVLVSGLVLMAMVKKKNS
```

TCB2 differs from TCB1 at four residues, underlined in the sequence above.

```
Human alpha chain constant region
                                          (SEQ ID NO: 15)
XIQNPDPAVYQLRDSKSSDKSVCLFTDFDSQTNVSQSKDSDVYITDKTVL

DMRSMDFKSNSAVAWSNKSDFACANAFNNSIIPEDTFFPSPESSCDVKLV

EKSFETDTNLNFQNLSVIGFRILLLKVAGFNLLMTLRLWSS.
```

In the sequence above, X can be any amino acid. In some examples, X=N

```
Human beta chain constant region
                                          (SEQ ID NO: 16)
EDLNKVFPPEVAVFEPSEAEISHTQKATLVCLATGFFPDHVELSWWVNGK

EVHSGVSTDPQPLKEQPALNDSRYCLSSRLRVSATFWQNPRNHFRCQVQF

YGLSENDEWTQDRAKPVTQIVSAEAWGRADCGFTSVSYQQGVLSATILYE

ILLGKATLYAVLVSALVLMAMVKRKD

Human beta chain constant region
                                          (SEQ ID NO: 17)
EDLKNVFPPEVAVFEPSEAEISHTQKATLVCLATGFYPDHVELSWWVNGK

EVHSGVSTDPQPLKEQPALNDSRYCLSSRLRVSATFWQNPRNHFRCQVQF

YGLSENDEWTQDRAKPVTQIVSAEAWGRADCGFTSESYQQGVLSATILYE

ILLGKATLYAVLVSALVLMAMVKRKDSRG
```

In view of the many possible embodiments to which the principles of the disclosed subject matter may be applied, it should be recognized that the illustrated embodiments are only examples of the disclosure and should not be taken as limiting the scope of the disclosure. Rather, the scope of the disclosure is defined by the following claims. We therefore claim all that comes within the scope and spirit of these claims.

The invention claimed is:

1. An isolated T cell receptor (TCR) having antigenic specificity for a mutant form of the rearranged during transfection (RET) proto-oncogene with a methionine to threonine substitution at position 918 of SEQ ID NO: 11, wherein the TCR comprises:

(a) an alpha chain variable region comprising a complementarity determining region 1 (CDR1), a CDR2 and a CDR3; and (b) a beta chain variable region comprising a CDR1, a CDR2 and a CDR3, wherein:

the alpha chain variable region CDR1, CDR2 and CDR3 respectively comprise residues 46-51, 69.75 and 110-120 of SEO ID NO: 2, and the beta chain variable region CDR1, CDR2 and CDR3 respectively comprise residues 46-50, 68-72 and 111-119 of SEQ ID NO: 4;

the alpha chain variable region CDR1, CDR2 and CDR3 respectively comprise residues 47-53, 71-78 and 113-123 of SEQ ID NO: 6, and the beta chain variable region CDR1, CDR2 and CDR3 respectively comprise residues 46-49, 67-72 and 111-123 of SEO ID NO: 8; or the alpha chain variable region CDR1, CDR2 and CDR3 respectively comprise residues 53-58, 76-82 and 117-129 of SEQ ID NO: 19, and the beta chain variable region CDR1, CDR2 and CDR3 respectively comprise residues 46-50, 68-73 and 112-126 of SEO ID NO: 21.

2. The isolated TCR of claim 1, wherein:

the amino acid sequence of the alpha chain variable region comprises SEQ ID NO: 2, and the amino acid sequence of the beta chain variable region comprises SEQ ID NO: 4;

the amino acid sequence of the alpha chain variable region comprises SEQ ID NO: 6, and the amino acid sequence of the beta chain variable region comprises SEQ ID NO: 8; or the amino acid sequence of the alpha chain variable region comprises SEQ ID NO: 19, and the amino acid sequence of the beta chain variable region comprises SEQ ID NO: 21.

3. The isolated TCR of claim 1, further comprising an alpha chain constant region and/or a beta chain constant region.

4. The isolated TCR of claim 3, wherein:

the alpha chain constant region is a murine alpha chain constant region or a human alpha chain constant region; and/or the beta chain constant region is a murine beta chain constant region or a human beta chain constant region.

5. The isolated TCR of claim 4, wherein:

the alpha chain constant region is a murine alpha chain constant region comprising an amino acid sequence at least 90% identical to SEQ ID NO: 12;

the alpha chain constant region is a murine alpha chain constant region, and the amino acid sequence of the murine alpha chain constant region comprises or consists of SEQ ID NO: 12, wherein the amino acid at position 1 is asparagine;

the beta chain constant region is a murine beta chain constant region comprising an amino acid sequence at least 90% identical to SEQ ID NO: 13 or SEQ ID NO: 14; and/or the beta chain constant region is a murine beta chain constant region, and the amino acid sequence of the murine beta chain constant region comprises or consists of SEQ ID NO: 13 or SEQ ID NO: 14.

6. An isolated nucleic acid molecule encoding the TCR of claim 1.

7. The isolated nucleic acid molecule of claim 6, wherein:

the nucleic acid molecule comprises the nucleotide sequence of SEQ ID NO: 1 and SEQ ID NO: 3, or degenerate variants thereof;

the nucleic acid molecule comprises the nucleotide sequence of SEQ ID NO: 5 and SEQ ID NO: 7, or degenerate variants thereof; or the nucleic acid molecule comprises the nucleotide sequence of SEQ ID NO: 18 and SEQ ID NO: 20, or degenerate variants thereof.

8. The isolated nucleic acid molecule of claim 6, further comprising a nucleotide sequence encoding an alpha chain constant region and/or a nucleotide sequence encoding a beta chain constant region.

9. The isolated nucleic acid molecule of claim 8, wherein the alpha chain constant region and/or the beta chain constant region are murine constant regions.

10. The isolated nucleic acid molecule of claim 9, wherein:

the alpha chain constant region is a murine alpha chain constant region comprising the amino acid sequence of SEQ ID NO: 12; and/or the beta chain constant region is a murine beta chain constant region comprising the amino acid sequence of SEQ ID NO: 13 or SEQ ID NO: 14.

11. The isolated nucleic acid molecule of claim 9, wherein the nucleotide sequence encoding the murine alpha chain constant region and/or the nucleotide sequence encoding the murine beta chain constant region is/are codon-optimized for expression in mammalian cells.

12. The isolated nucleic acid molecule of claim 6, further comprising a nucleotide sequence encoding a P2A linker sequence.

13. The isolated nucleic acid molecule of claim 12, comprising in the 5' to 3' direction:

the alpha chain variable region, the alpha chain constant region, the P2A linker sequence, the beta chain variable region and the beta chain constant region; or the beta chain variable region, the beta chain constant region, the P2A linker sequence, the alpha chain variable region and the alpha chain constant region.

14. The nucleic acid molecule of claim 6 operably linked to a promoter.

15. A vector comprising the nucleic acid molecule of claim 6.

16. The vector of claim 15, which is a viral vector or a plasmid vector.

17. The vector of claim 16, wherein the viral vector is a retroviral vector.

18. An isolated host cell comprising the nucleic acid molecule of claim 6.

19. The isolated host cell of claim 18, wherein the host cell is a human T cell.

20. A composition comprising a pharmaceutically acceptable carrier and the isolated host cell of claim 18.

21. A method of treating a cancer expressing M918T RET in a subject, comprising administering to the subject a therapeutically effective amount of the isolated host cell of claim 18, wherein the isolated host cell is a T cell.

22. The method of claim 21, wherein the cancer is medullary thyroid cancer.

23. The method of claim 21, wherein the host cell is autologous to the subject.

24. The method of claim 21, wherein the subject expresses HLA-DPA1*01:03, HLA-DPB1*04:01 and/or HLA-DPB1*04:02.

25. A method of making transduced T cells expressing a T cell receptor (TCR) having antigenic specificity for a mutant form of the rearranged during transfection (RET) proto-oncogene with a methionine to threonine substitution at position 918 of SEQ ID NO: 11, the method comprising:

obtaining a population of lymphocytes from a subject;

contacting the population of lymphocytes with an anti-CD3 antibody and interleukin-2 to produce a population of activated T cells; and transducing the population of activated T cells with the vector of claim 15, thereby producing the transduced T cells.

26. The method of claim 21, wherein the isolated host cell comprises a nucleic acid molecule comprising the nucleotide sequence of SEQ ID NO: 18 and SEQ ID NO: 20, or degenerate variants thereof.

* * * * *

SEQUENCE LISTING

```
<160> NUMBER OF SEQ ID NOS: 21

<210> SEQ ID NO 1
<211> LENGTH: 394
<212> TYPE: DNA
<213> ORGANISM: Homo sapiens

<400> SEQUENCE: 1

atgaactatt ctccaggctt agtatctctg atactcttac tgcttggaag aacccgtgga      60

aattcagtga cccagatgga agggccagtg actctctcag aagaggcctt cctgactata     120

aactgcacgt acacagccac aggataccct tccctttctt ggtatgtcca atatcctgga     180

gaaggtctac agctcctcct gaaagccacg aaggctgatg acaagggaag caacaaaggt     240

tttgaagcca cataccgtaa agaaaccact tctttccact tggagaaagg ctcagttcaa     300

gtgtcagact cagcggtgta cttctgtgct ctgagtgaga acgccggtaa ccagttctat     360

tttgggacag ggacaagttt gacggtcatt ccaa                                 394


<210> SEQ ID NO 2
<211> LENGTH: 131
<212> TYPE: PRT
<213> ORGANISM: Homo sapiens

<400> SEQUENCE: 2
```

Met Asn Tyr Ser Pro Gly Leu Val Ser Leu Ile Leu Leu Leu Leu Gly
1 5 10 15

Arg Thr Arg Gly Asn Ser Val Thr Gln Met Glu Gly Pro Val Thr Leu
20 25 30

Ser Glu Glu Ala Phe Leu Thr Ile Asn Cys Thr Tyr Thr Ala Thr Gly
35 40 45

Tyr Pro Ser Leu Phe Trp Tyr Val Gln Tyr Pro Gly Glu Gly Leu Gln
50 55 60

Leu Leu Leu Lys Ala Thr Lys Ala Asp Asp Lys Gly Ser Asn Lys Gly
65 70 75 80

Phe Glu Ala Thr Tyr Arg Lys Glu Thr Thr Ser Phe His Leu Glu Lys
85 90 95

Gly Ser Val Gln Val Ser Asp Ser Ala Val Tyr Phe Cys Ala Leu Ser
100 105 110

Glu Asn Ala Gly Asn Gln Phe Tyr Phe Gly Thr Gly Thr Ser Leu Thr
115 120 125

Val Ile Pro
130

<210> SEQ ID NO 3
<211> LENGTH: 388
<212> TYPE: DNA
<213> ORGANISM: Homo sapiens

<400> SEQUENCE: 3
atgagcatcg gcctcctgtg ctgtgcagcc ttgtctctcc tgtgggcagg tccagtgaat 60
gctggtgtca ctcagacccc aaaattccag gtcctgaaga caggacagag catgacactg 120
cagtgtgccc aggatatgaa ccatgaatac atgtcctggt atcgacaaga cccaggcatg 180
gggctgaggc tgattcatta ctcagttggt gctggtatca ctgaccaagg agaagtcccc 240
aatggctaca atgtctccag atcaaccaca gaggatttcc cgctcaggct gctgtcggct 300
gctccctccc agacatctgt gtacttctgt gccagcagcc gagggaatac gcagtatttt 360
ggcccaggca cccggctgac agtgctcg 388

<210> SEQ ID NO 4
<211> LENGTH: 129
<212> TYPE: PRT
<213> ORGANISM: Homo sapiens

<400> SEQUENCE: 4

Met Ser Ile Gly Leu Leu Cys Cys Ala Ala Leu Ser Leu Leu Trp Ala
1 5 10 15

Gly Pro Val Asn Ala Gly Val Thr Gln Thr Pro Lys Phe Gln Val Leu
20 25 30

Lys Thr Gly Gln Ser Met Thr Leu Gln Cys Ala Gln Asp Met Asn His
35 40 45

Glu Tyr Met Ser Trp Tyr Arg Gln Asp Pro Gly Met Gly Leu Arg Leu
50 55 60

Ile His Tyr Ser Val Gly Ala Gly Ile Thr Asp Gln Gly Glu Val Pro
65 70 75 80

Asn Gly Tyr Asn Val Ser Arg Ser Thr Thr Glu Asp Phe Pro Leu Arg
85 90 95

Leu Leu Ser Ala Ala Pro Ser Gln Thr Ser Val Tyr Phe Cys Ala Ser
100 105 110

```
Ser Arg Gly Asn Thr Gln Tyr Phe Gly Pro Gly Thr Arg Leu Thr Val
        115                 120                 125

Leu


<210> SEQ ID NO 5
<211> LENGTH: 403
<212> TYPE: DNA
<213> ORGANISM: Homo sapiens

<400> SEQUENCE: 5

atgtcacttt ctagcctgct gaaggtggtc acagcttcac tgtggctagg acctggcatt      60

gcccagaaga taactcaaac ccaaccagga atgttcgtgc aggaaaagga ggctgtgact     120

ctggactgca catatgacac cagtgatcaa agttatggtc tattctggta caagcagccc     180

agcagtgggg aaatgatttt tcttatttat caggggtctt atgacgagca aaatgcaaca     240

gaaggtcgct actcattgaa tttccagaag gcaagaaaat ccgccaacct tgtcatctcc     300

gcttcacaac tgggggactc agcaatgtat ttctgtgcaa tgagagaggg cgatggtgat     360

gacatgcgct ttggagcagg gaccagactg acagtaaaac caa                      403


<210> SEQ ID NO 6
<211> LENGTH: 134
<212> TYPE: PRT
<213> ORGANISM: Homo sapiens

<400> SEQUENCE: 6

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Gly Asp Gly Asp Asp Met Arg Phe Gly Ala Gly Thr
        115                 120                 125

Arg Leu Thr Val Lys Pro
    130


<210> SEQ ID NO 7
<211> LENGTH: 409
<212> TYPE: DNA
<213> ORGANISM: Homo sapiens

<400> SEQUENCE: 7

atggatacct ggctcgtatg ctgggcaatt tttagtctct tgaaagcagg actcacagaa      60

cctgaagtca cccagactcc cagccatcag gtcacacaga tgggacagga agtgatcttg     120

cgctgtgtcc ccatctctaa tcacttatac ttctattggt acagacaaat cttggggcag     180

aaagtcgagt ttctggtttc cttttataat aatgaaatct cagagaagtc tgaaatattc     240

gatgatcaat tctcagttga aaggcctgat ggatcaaatt tcactctgaa gatccggtcc     300
```

```
acaaagctgg aggactcagc catgtacttc tgtgccagca gttctcagat tcagacggtc    360

atgaacactg aagctttctt tggacaaggc accagactca cagttgtag                409


<210> SEQ ID NO 8
<211> LENGTH: 135
<212> TYPE: PRT
<213> ORGANISM: Homo sapiens

<400> SEQUENCE: 8

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Leu Arg Cys Val Pro Ile Ser Asn His Leu
        35                  40                  45

Tyr Phe Tyr Trp Tyr Arg Gln Ile Leu Gly Gln Lys Val Glu Phe Leu
    50                  55                  60

Val Ser Phe Tyr Asn Asn Glu Ile Ser Glu Lys Ser Glu Ile Phe Asp
65                  70                  75                  80

Asp Gln Phe Ser Val Glu Arg Pro Asp Gly Ser Asn Phe Thr Leu Lys
                85                  90                  95

Ile Arg Ser Thr Lys Leu Glu Asp Ser Ala Met Tyr Phe Cys Ala Ser
            100                 105                 110

Ser Ser Gln Ile Gln Thr Val Met Asn Thr Glu Ala Phe Phe Gly Gln
        115                 120                 125

Gly Thr Arg Leu Thr Val Val
    130                 135


<210> SEQ ID NO 9
<211> LENGTH: 25
<212> TYPE: PRT
<213> ORGANISM: Homo sapiens

<400> SEQUENCE: 9

Val Lys Arg Ser Gln Gly Arg Ile Pro Val Lys Trp Met Ala Ile Glu
1               5                   10                  15

Ser Leu Phe Asp His Ile Tyr Thr Thr
            20                  25


<210> SEQ ID NO 10
<211> LENGTH: 25
<212> TYPE: PRT
<213> ORGANISM: Homo sapiens

<400> SEQUENCE: 10

Val Lys Arg Ser Gln Gly Arg Ile Pro Val Lys Trp Thr Ala Ile Glu
1               5                   10                  15

Ser Leu Phe Asp His Ile Tyr Thr Thr
            20                  25


<210> SEQ ID NO 11
<211> LENGTH: 1114
<212> TYPE: PRT
<213> ORGANISM: Homo sapiens

<400> SEQUENCE: 11

Met Ala Lys Ala Thr Ser Gly Ala Ala Gly Leu Arg Leu Leu Leu Leu
1               5                   10                  15
```

```
Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
```

-continued

```
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
        595                 600                 605

Cys Asn Cys Phe Pro Glu Glu Glu Lys Cys Phe Cys Glu Pro Glu Asp
    610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
    690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
    770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
    850                 855                 860
```

```
Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp  Ile Ser Lys Asp Leu  Glu Lys Met
        995                 1000                1005

Met Val  Lys Arg Arg Asp Tyr  Leu Asp Leu Ala Ala  Ser Thr Pro
    1010                1015                1020

Ser Asp  Ser Leu Ile Tyr Asp  Asp Gly Leu Ser Glu  Glu Glu Thr
    1025                1030                1035

Pro Leu  Val Asp Cys Asn Asn  Ala Pro Leu Pro Arg  Ala Leu Pro
    1040                1045                1050

Ser Thr  Trp Ile Glu Asn Lys  Leu Tyr Gly Met Ser  Asp Pro Asn
    1055                1060                1065

Trp Pro  Gly Glu Ser Pro Val  Pro Leu Thr Arg Ala  Asp Gly Thr
    1070                1075                1080

Asn Thr  Gly Phe Pro Arg Tyr  Pro Asn Asp Ser Val  Tyr Ala Asn
    1085                1090                1095

Trp Met  Leu Ser Pro Ser Ala  Ala Lys Leu Met Asp  Thr Phe Asp
    1100                1105                1110

Ser
```

```
<210> SEQ ID NO 12
<211> LENGTH: 137
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is Asn or Asp

<400> SEQUENCE: 12

Xaa Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80
```

```
Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 13
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 13

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170


<210> SEQ ID NO 14
<211> LENGTH: 173
<212> TYPE: PRT
<213> ORGANISM: Mus musculus

<400> SEQUENCE: 14

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80
```

```
Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr His Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Lys Asn Ser
                165                 170


<210> SEQ ID NO 15
<211> LENGTH: 141
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa is any amino acid

<400> SEQUENCE: 15

Xaa Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140


<210> SEQ ID NO 16
<211> LENGTH: 176
<212> TYPE: PRT
<213> ORGANISM: Homo sapiens

<400> SEQUENCE: 16

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60
```

-continued

```
Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175


<210> SEQ ID NO 17
<211> LENGTH: 179
<212> TYPE: PRT
<213> ORGANISM: Homo sapiens

<400> SEQUENCE: 17

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly


<210> SEQ ID NO 18
<211> LENGTH: 421
<212> TYPE: DNA
<213> ORGANISM: Homo sapiens

<400> SEQUENCE: 18

atggccatgc tcctgggggc atcagtgctg attctgtggc ttcagccaga ctgggtaaac      60

agtcaacaga agaatgatga ccagcaagtt aagcaaaatt caccatccct gagcgtccag     120

gaaggaagaa tttctattct gaactgtgac tatactaaca gcatgtttga ttatttccta     180

tggtacaaaa aataccctgc tgaaggtcct acattcctga tatctataag ttccattaag     240
```

```
gataaaaatg aagatggaag attcactgtc ttcttaaaca aaagtgccaa gcacctctct    300

ctgcacattg tgccctccca gcctggagac tctgcagtgt acttctgtgc agcaagcggc    360

catggaggaa gccaaggaaa tctcatcttt ggaaaaggca ctaaactctc tgttaaacca    420

a                                                                    421
```

<210> SEQ ID NO 19
<211> LENGTH: 140
<212> TYPE: PRT
<213> ORGANISM: Homo sapiens

<400> SEQUENCE: 19

```
Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Gly His Gly Gly Ser Gln Gly Asn Leu
        115                 120                 125

Ile Phe Gly Lys Gly Thr Lys Leu Ser Val Lys Pro
    130                 135                 140
```

<210> SEQ ID NO 20
<211> LENGTH: 409
<212> TYPE: DNA
<213> ORGANISM: Homo sapiens

<400> SEQUENCE: 20

```
atgggcacca ggctcctctg ctgggtggtc ctgggtttcc tagggacaga tcacacaggt     60

gctggagtct cccagtcccc taggtacaaa gtcgcaaaga gaggacagga tgtagctctc    120

aggtgtgatc caatttcggg tcatgtatcc ctttttttggt accaacaggc cctggggcag    180

gggccagagt ttctgactta tttccagaat gaagctcaac tagacaaatc ggggctgccc    240

agtgatcgct tctttgcaga aaggcctgag ggatccgtct ccactctgaa gatccagcgc    300

acacagcagg aggactccgc cgtgtatctc tgtgccagca gcttaaggtt tttgggacag    360

ggctcctacg agcagtactt cgggccgggc accaggctca cggtcacag                409
```

<210> SEQ ID NO 21
<211> LENGTH: 136
<212> TYPE: PRT
<213> ORGANISM: Homo sapiens

<400> SEQUENCE: 21

```
Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30
```

-continued

```
Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
    50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                  90                  95

Lys Ile Gln Arg Thr Gln Gln Glu Asp Ser Ala Val Tyr Leu Cys Ala
            100                 105                 110

Ser Ser Leu Arg Phe Leu Gly Gln Gly Ser Tyr Glu Gln Tyr Phe Gly
        115                 120                 125

Pro Gly Thr Arg Leu Thr Val Thr
    130                 135
```